(12) United States Patent
Goepfert et al.

(10) Patent No.: US 10,151,002 B2
(45) Date of Patent: Dec. 11, 2018

(54) METHOD FOR THE SELECTION OF A LONG-TERM PRODUCING CELL

(71) Applicant: HOFFMANN-LA ROCHE INC., Nutley, NJ (US)

(72) Inventors: Ulrich Goepfert, Penzberg (DE); Andrea Osterlehner, Penzberg (DE); Silke Lueckel, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/879,347

(22) Filed: Oct. 9, 2015

(65) Prior Publication Data

US 2016/0130667 A1 May 12, 2016

Related U.S. Application Data

(63) Continuation of application No. 13/640,053, filed as application No. PCT/EP2011/055835 on Apr. 13, 2011.

(30) Foreign Application Priority Data

Apr. 14, 2010 (EP) ..................................... 10003969

(51) Int. Cl.
| | | |
|---|---|---|
| C12Q 1/68 | (2018.01) | |
| C12P 21/00 | (2006.01) | |
| C12Q 1/6888 | (2018.01) | |
| C07K 16/00 | (2006.01) | |
| C12P 21/02 | (2006.01) | |
| C12Q 1/6827 | (2018.01) | |
| C12Q 1/6881 | (2018.01) | |

(52) U.S. Cl.
CPC ............ *C12Q 1/6888* (2013.01); *C07K 16/00* (2013.01); *C12P 21/00* (2013.01); *C12P 21/02* (2013.01); *C12Q 1/6827* (2013.01); *C12Q 1/6881* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 5,562,803 A | * | 10/1996 | Wang ........................ | D21C 5/02 162/5 |
| 6,030,638 A | | 2/2000 | Brigham et al. | |
| 2002/0094967 A1 | | 7/2002 | Antoniou et al. | |
| 2009/0191545 A1 | | 7/2009 | Dorai | |

FOREIGN PATENT DOCUMENTS

| | | |
|---|---|---|
| WO | 2006/089152 A2 | 8/2006 |
| WO | 2008/018855 A2 | 2/2008 |
| WO | 2008/085956 A2 | 7/2008 |
| WO | 2008/085962 A2 | 7/2008 |

OTHER PUBLICATIONS

Brooks et al. (2004) Transcriptional silencing is associated with extensive methylation of the CMV promoter following adenoviral gene delivery to muscle. The Journal of Gene Medicine, 6:395-404.*
Escher et al. (2005) Demethylation using the epigenetic modifier, 5-azacytidine, increases the efficiency of transient transfection of macrophages. Journal of Lipid Research, 46:356-365.*
Everett et al. (2004) Strain-specific rate of shutdown of CMVenhancer activity in murine liver confirmed by use of persistent [E1-, E2b-] adenoviral vectors. Virology, 325:96-105.*
Thisted, R. (1998) What is a P-Value? The University of Chicago, 6 pages, available from <http://www.stat.uchicago.edu/~thisted>.*
Wray et al. (2007) The evolutionary significance of cis-regulatory mutations. Nature, 8:206-216.*
Brooks et al., "Transcriptional silencing is associated with extensive methylation of the CMV promoter following adenoviral gene delivery to muscle," J. Gene Med. 6(4):395-404 (2004).
Chusainow et al., "A study of monoclonal antibody-producing CHO cell lines: what makes a stable high producer?" Biotechnol. Bioeng. 102(4):1182-1196 (2008).
Dickenson et al., "VEZF1 elements mediate protection from DNA methylation," PLoS Genet. 6(1):e1000804 (2010) (Epub Jan. 8, 2010). (pp. 1-16).
Escher et al., "Demethylation using the epigenetic modifier, 5-azacytidine, increases the efficiency of transient transfection of macrophages," J. Lipid Res. 46(2):356-365 (2004) (Epub Nov. 1, 2004).
European Search Report for European Application EP 10003969.2, (dated Sep. 15, 2010).
Everett et al., "Strain-specific rate of shutdown of CMV enhancer activity in murine liver confirmed by use of persistent [E1(-), E2b(-)] adenoviral vectors," Virology 325(1):96-105 (2004).
Garrick et al., "Repeat-induced gene silencing in mammals," Nat. Genet. 18(1):56-59 (1998).
Hacker et al., "25 years of recombinant proteins from reactor-grown cells—where do we go from here?" Biotechnol. Adv. 27(6):1023-1027 (2009) (Epub May 20, 2009).
International Search Report for International Application No. PCT/EP2011/055835, (dated Jul. 15, 2011).
Kong et al., "Transgene expression is associated with copy number and cytomegalovirus promoter methylation in transgenic pigs," PLoS One 4(8):e6679 (2009).
Kristensen et al., "PCR-based methods for detecting single-locus DNA methylation biomarkers in cancer diagnostics, prognostics, and response to treatment," Clin. Chem. 55(8):1471-1483 (2009) (Epub Jun. 11, 2009).
Mielke et al., "Stabilized, long-term expression of heterodimeric proteins from tricistronic mRNA," Gene 254(1-2):1-8 (2000).

(Continued)

*Primary Examiner* — Neil P Hammell
(74) *Attorney, Agent, or Firm* — Jones Day

(57) ABSTRACT

Herein is reported a method for determining methylation of a promoter nucleic acid operably linked to a nucleic acid encoding a polypeptide and thereby determining the long-term productivity of a cell. Also an aspect is a method for selecting a cell for producing a polypeptide by determining the methylation of the promoter nucleic acid operably linked to the structural gene encoding the polypeptide.

7 Claims, 24 Drawing Sheets

Specification includes a Sequence Listing.

(56) References Cited

OTHER PUBLICATIONS

Prösch et al., "Inactivation of the very strong HCMV immediate early promoter by DNA CpG methylation in vitro," Biol. Chem. Hoppe-Seyler 377(3):195-201 (1996).
Recillas-Targa et al., "Position-effect protection and enhancer blocking by the chicken beta-globin insulator are separable activities," Proc. Natl. Acad. Sci. U.S.A. 99(10):6883-6838 (2002).
The English translation of the Japanese Office Action, dated Jun. 17, 2015, in the corresponding Japanese Application No. 2013-504262.
Written Opinion of the International Searching Authority for International Application No. PCT/EP2011/055835, (dated Jul. 15, 2011).
Wurm, "Production of recombinant protein therapeutics in cultivated mammalian cells," Nat. Biotechnol. 22(11):1393-1398 (2004).
Yang et al., "DNA methylation contributes to loss in productivity of monoclonal antibody-producing CHO cell lines," J. Biotechnol. 147(3-4):180-185 (2010) (Epub Apr. 27, 2010).

\* cited by examiner

METHOD FOR THE SELECTION OF A LONG-TERM PRODUCING CELL

The herein reported method is in the field of cell selection and polypeptide expression. In more detail, herein is reported a method for the selection of a long-term polypeptide expressing or secreting cell based on the detection of the methylation of the nucleic acid of the promoter operably linked to the structural gene encoding the polypeptide.

BACKGROUND OF THE INVENTION

Enzymatic methylation of cytosine bases at carbon 5 resulting in 5-methyl-cytosine is a DNA modification found in prokaryotes as well as eukaryotes. In eukaryotic cells it is well known as a fundamental epigenetic mechanism resulting in gene silencing. Methylation occurs specifically at CpG dinucleotides which are frequently found within promoter regions. Outside promoters, CpG sites are rare. Methylated promotors are silent i.e. transcriptionally inactive so that the gene is not expressed. Methylated DNA recruits methyl-DNA binding proteins which form a platform for other factors like HDACs which modify and condense the chromatin.

Gene silencing by promoter methylation has been reported not only for autologous genes but also for recombinant gene constructs (Escher, G., et al., J. Lipid Res. 46 (2005) 356-365; Brooks, A. R., et al., J. Gen. Med. 6 (2004) 395-404). Bisulfite treatment of DNA is a method suitable to discriminate between methylated and non-methylated CpG sites. Under the conditions used, cytosine but not 5-methyl-cytosine is deaminated at C4 and thereby converted to uracil. Complementary DNA strands are thereby converted into two strands, A and B, which are no longer complementary.

Barnes, L. M., et al. (Biotechnol. Bioeng. 96 (2006) 337-348) report that the LC/HC mRNA level is for NSO cell a marker for long-term stability. Chusainow, J., et al. (Biotechnol. Bioeng. 102 (2009) 1182-1196) and Jiang, Z., et al. (Biotechnol. Prog. 22 (2006) 313-318) report that higher LC/HC mRNA levels for MTX treated cells. Lee, C. J., et al. (Biotechnol. Bioeng. 102 (2008) 1107-1118) report the screening of cells based on the HC mRNA level.

Escher et al. (see above) report CMV promotor silencing in transiently transfected macrophages. CMV promoter silencing in vivo with adenoviruses is reported by Brooks et al. (see above).

VEZF1 elements mediate protection from DNA methylation is reported by Dickson, J., et al. (PLoS Genetics 6 (2001) e1000804). Mielke, C., et al. (Gene 254 (2000) 1-8) report stabilized, long-term expression of heterodimeric proteins from tricistronic mRNA. Strain-specific rate of shutdown of CMV enhancer activity in murine liver confirmed by use of persistent adenoviral vectors is reported by Everett, R. S., et al. (J. Virol. 325 (2004) 96-105). Proesch, S., et al. (Biol. Chem. Hoppe-Seyler 377 (1996) 195-201) report inactivation of the very strong HCMV immediate early promoter by DNA CPG methylation in vitro. PCR-based methods for detecting single-locus DNA methylation biomarkers in cancer diagnostics, prognostics, and response to treatment is reported by Kristensen, L. S. and Hansen, L. L. (Clin. Chem. 55 (2009) 1471-1483). Recillas-Targa, F., et al. (Proc. Natl. Acad. Sci. USA 99 (2002) 6883-6888) report that position-effect protection and enhancer blocking by the chicken beta-globin insulator are separable activities.

SUMMARY OF THE INVENTION

It has been found that the determination of the degree of methylation of a specific CpG site in the promoter nucleic acid operably linked to a structural gene encoding a polypeptide in a cell or cell line used for the production of the respective polypeptide can be used to predict a decrease in productivity during long-term cultivation.

As an aspect herein is reported a method for selecting a cell comprising the following steps:
  a) identifying a CpG-site in a promoter nucleic acid with a method comprising the following steps:
    1) separately isolating the DNA from at least 10 cells of a cultivation of a cell that has a production rate of a polypeptide that is after a cultivation time of 30 generations of the cell in the absence of a selection agent less than 90% of the production rate of the cell after the first generation of the cultivation,
    2) modifying the cytosine of the isolated DNA by bisulfite treatment,
    3) identifying a CpG site within the promoter nucleic acid operably linked to the structural gene encoding the polypeptide with a methylation frequency of at least 0.2 based on the DNA obtained in step 2) and thereby identifying a CpG-site,
  b) providing at least one cell comprising a nucleic acid comprising a structural gene encoding a polypeptide operably linked to a promoter nucleic acid which is the same as that of step a),
  c) determining the methylation frequency of the CpG-site identified in step a) for each of the at least one cell of step b) based on at least 10 copies of the promoter nucleic acid or 10 cells obtained from a cultivation thereof,
  d) selecting a cell in which the methylation frequency as determined in step c) is below twice the average value obtained by determining the methylation of a cytosine at a non-CpG-site, or selecting a cell in which the methylation frequency as determined in step c) is below 5%.

Another aspect as reported herein is a method for selecting a cell comprising the following steps:
  a) determining for each of at least one cell comprising a nucleic acid, which comprises a structural gene encoding a polypeptide operably linked to a promoter nucleic acid that has the nucleic acid sequence of SEQ ID NO: 01, the methylation frequency of a CpG-site at a position selected from positions 80, 96, 425, 437, 563 and 591 of SEQ ID NO: 01 based on the methylation determined for at least 10 copies of the promoter nucleic acid or in at least 10 cells obtained from a cultivation of each cell,
  b) selecting a cell in which the methylation frequency as determined is below 5%.

In one embodiment the determining comprises the following steps:
  1) isolating the DNA from each of the cells,
  2) performing for each isolated DNA individually a methylation specific polymerase chain reaction,
  3) determining with the results obtained in step 2) the methylation frequency of the CpG-site.

In another embodiment step 2) is the following step:
  2) performing for each isolated DNA individually a polymerase chain reaction with a methylation specific primer and a universal primer.

In also an embodiment step 2) is the following step:
  2) individually digesting the isolated DNA with a restriction enzyme and performing a polymerase chain reaction for each of the digested DNA with a methylation specific primer and a universal primer.

In one embodiment the promoter nucleic acid has the sequence of SEQ ID NO: 01 or comprises a fragment thereof or a variant thereof and the CpG-site is selected from position 80, 96, 425, 437, 563 and 591 of SEQ ID NO: 01 or a thereto corresponding position in a fragment or variant thereof. In another embodiment the primer are independently of each other selected from the group consisting of SEQ ID NO: 06 to 20. In a further embodiment a primer is selected from the group consisting of SEQ ID NO: 11, 14 and 15, the universal primer has the sequence of SEQ ID NO: 09 and a methylation specific primer is selected from the group consisting of SEQ ID NO: 17, 18 and 19. In also an embodiment the universal primer have the sequence of SEQ ID NO: 09 and 11 and the methylation specific primer have the sequence of SEQ ID NO: 11 and 18.

Also an aspect as reported herein is a method for the production of a polypeptide comprising the following steps:
  a) selecting a cell with a method as reported herein,
  b) cultivating the selected cell, and
  c) recovering the polypeptide from the cultivation medium and/or the cell and thereby producing a polypeptide.

In one embodiment the method comprises prior to step a) the following steps:
  a-3) providing a cell,
  a-2) transfecting the provided cell with a nucleic acid containing a structural gene encoding the polypeptide operably linked to a promoter nucleic acid,
  a-1) i) optionally cultivating and propagating the transfected cell in the presence of a selection agent, ii) single depositing the cells, and iii) cultivating the single deposited transfected cells in the presence of a selection agent.

A further aspect as reported herein is a kit comprising
  a) a reagent for the modification of non-methylated cytosine in a CpG-site, and
  b) a primer selected from SEQ ID NO: 13, 16, 17, 18, 19 and 20.

In one embodiment of the aspects as reported herein the cell is a cell clone.

DETAILED DESCRIPTION OF THE INVENTION

Mammalian cell lines for recombinant protein production need to maintain productivity over extended cultivation times. Long term stability studies are time and resource intensive, but are widely performed to identify and eliminate unstable candidates during cell line development. Production instability of manufacturing cell lines can be associated with methylation and silencing of the heterologous promoter. CpG dinucleotides within the human cytomegalovirus major immediate early promoter/enhancer (hCMV-MIE) have been identified herein that are frequently methylated in unstable antibody-producing Chinese hamster ovary (CHO) cell lines. A methylation-specific real-time qPCR has been established to allow for the rapid and sensitive measurement of hCMV-MIE methylation in multiple cell lines and to provide evidence that hCMV-MIE methylation and transgene copy numbers can be used as early markers to predict production stability of recombinant CHO cell lines. These markers should provide the opportunity to enrich stable producers early in cell line development.

Thus, herein is reported a method for the selection of a cell as well as a method for the production of a polypeptide. The selected cell and also the cell used for the production of a polypeptide is a long-term producing cell. Such a cell can be selected as reported herein based on the methylation of the promoter operably linked to the structural gene encoding the polypeptide.

The term "almost" denotes that the value following this expression is a center value with certain variability. In one embodiment the variability is of ±20% of the value, in another embodiment the variability is of ±10%, and in a further embodiment the variability is of 5%. Thus, the term almost constant denotes that a value is in one embodiment in the range of from 80% to 120%, in another embodiment in the range of from 90% to 110%, and in a further embodiment in the range of from 95% to 105%.

The term "antibody" denotes a molecule comprising at least two so called light chain polypeptides (light chain) and two so called heavy chain polypeptides (heavy chain). Each of the heavy and light chain polypeptides comprises a variable domain (variable region) (generally the amino terminal portion of the polypeptide chain) comprising binding regions that are able to interact with an antigen. Each of the heavy and light chain polypeptides also comprises a constant region (generally the carboxy-terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

Depending on the amino acid sequence of the constant region of the heavy chains, antibodies are divided in different classes: IgA class, IgD class, IgE class, IgG class, and IgM class. Some of these classes are further divided into subclasses (isotypes), i.e. IgG in IgG1, IgG2, IgG3, and IgG4, or IgA in IgA1 and IgA2. According to the class to which an antibody belongs the heavy chain constant regions are called α (IgA), δ (IgD), ε (IgE), γ (IgG), and μ (IgM), respectively. In one embodiment the antibody is an antibody of the IgG class. In another embodiment the antibody has a human constant region or a constant region derived from human origin. In a further embodiment the antibody is of the IgG4 subclass or the IgG1, IgG2, or IgG3 subclass, which is modified in such a way that no Fcγ receptor (e.g. FcγRIIIa) binding and/or no C1q binding can be detected. In one embodiment the antibody is of the human IgG4 subclass or a mutated human IgG subclass. In one embodiment the antibody is of the human IgG subclass with mutations L234A and L235A. In another embodiment the antibody is in regard to Fcγ receptor binding of IgG4 subclass or of IgG1 or IgG2 subclass, with a mutation in L234, L235, and/or D265, and/or contains the PVA236 mutation. In a further embodiment the antibody has a mutation selected from S228P, L234A, L235A, L235E, SPLE (S228P and L235E), and/or PVA236 (PVA236 means that the amino acid sequence ELLG (given in one letter amino acid code) from amino acid position 233 to 236 of IgG1 or EFLG of IgG4 is replaced by PVA). In one embodiment the antibody is of the IgG4 subclass and has the mutation S228P of IgG4, or the antibody is of the IgG1 subclass and has the mutations L234A and L235A.

The variable domain of an immunoglobulin's light or heavy chain in turn comprises different segments, i.e. four framework regions (FR) and three hypervariable regions (CDR).

The term "bisulfite treatment" denotes a reaction for the conversion of cytosine bases in a nucleic acid to uracil bases in the presence of bisulfite ions whereby 5-methyl-cytosine bases are not significantly converted. This reaction for the detection of methylated cytosine is described in detail by Frommer et al. (Frommer, M., et al., Proc. Natl. Acad. Sci. USA 89 (1992) 1827-1831) and Grigg and Clark (Grigg, G. W. and Clark, S., Bioessays 16 (1994) 431-436; Grigg, G. W., DNA Seq. 6 (1996) 189-198). The bisulfite reaction contains a deamination step and a desulfonation step which can be conducted separately or simultaneously. The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases.

The term "cell" denotes a cell into which a nucleic acid, e.g. encoding a, optionally heterologous, polypeptide, can be or is introduced/transfected. The term "cell" includes both prokaryotic cells, which are used for propagation of plasmids, and eukaryotic cells, which are used for the expression of a nucleic acid. In one embodiment the cell is a eukaryotic cell and in a further embodiment the eukaryotic cell is a mammalian cell. In another embodiment the mammalian cell is selected from the group of mammalian cells comprising CHO cells (e.g. CHO K1, CHO DG44), BHK cells, NSO cells, SP2/0 cells, HEK 293 cells, HEK 293 EBNA cells, PER.C6® cells, and COS cells. As used herein, the expression "cell" includes the subject cell and its progeny. Thus, the term "cell" denotes the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The term "CpG-site" denotes the dinucleotide CG within a nucleic acid that can be recognized by the methylating enzymes of a cell and wherein the cytosine can be converted to 5-methyl cytosine. In one embodiment the CpG-site is within a promoter nucleic acid.

The term "expression cassette" denotes a construct that contains the necessary regulatory elements, such as promoter and polyadenylation site, for expression of at least the contained nucleic acid in a cell.

The term "expression plasmid" denotes a nucleic acid providing all required elements for the expression of the comprised structural gene(s) in a cell. Typically, an expression plasmid comprises a prokaryotic plasmid propagation unit, e.g. for *E. coli*, comprising an origin of replication, and a selection marker, an eukaryotic selection marker, and one or more expression cassettes for the expression of the structural gene(s) of interest each comprising a promoter nucleic acid, a structural gene, and a transcription terminator including a polyadenylation signal. Gene expression is usually placed under the control of a promoter nucleic acid, and such a structural gene is said to be "operably linked to" the promoter nucleic acid. Similarly, a regulatory element and a core promoter nucleic acid are operably linked if the regulatory element modulates the activity of the core promoter nucleic acid.

The term "generation time" denotes the time required by a cell to divide and to produce a daughter cell. Thus, a cell that has divided once has an age of one generation. The term "generation" denotes the number of cell division of a cell.

The term "high frequency" denotes that at this methylation site the cytosine is methylated more often than at other methylation sites based on the analysis of the methylation of a statistical significant number of individual cells or DNA clones, respectively. This statistical significant number is in one embodiment at least 10 individual cells or DNA clones, respectively, in a further embodiment at least 15 individual cells or DNA clones, respectively, and in another embodiment at least 20 individual cells or DNA clones, respectively. In one embodiment at maximum 400 cells or DNA clones, respectively, are analyzed.

The term "long-term producing cell" denotes a cell that produces a polypeptide, in one embodiment a heterologous polypeptide, whereby the specific production rate of the cell is almost constant for at least 30 generations. In one embodiment the long-term producing cell has a specific production rate that is almost constant for at least 30 generations, in another embodiment for at least 45 generations and in a further embodiment for at least 60 generations. In one embodiment the long-term producing cell has a specific production rate that is almost constant for up to 60 generations, in a further embodiment for up to 75 generations and in another embodiment for up to 90 generations.

The term "methylation" denotes a process within a cell that has been transfected with a nucleic acid comprising a structural gene encoding a polypeptide operably linked to a promoter in which a cytosine of the promoter nucleic acid is converted to 5-methyl cytosine. A promoter nucleic acid in which at least one cytosine is converted to 5-methyl cytosine is denoted as "methylated" nucleic acid.

The term "operably linked" denotes a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "polypeptide" denotes a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "variant" of a promoter nucleic acid denotes that within the promoter nucleic acid one or more nucleotides are changed without interfering with the function of the promoter nucleic acid. Such a change may be for removing or introducing a restriction site.

The term "producing" denotes the expression of a structural gene inserted into an expression cassette in a cell. The term includes the processes of transcription and translation of nucleic acid. Producing is performed in appropriate prokaryotic or eukaryotic cells and the expressed, i.e. produced, polypeptide can be recovered from the cells after lysis or from the culture supernatant.

The term "promoter nucleic acid" denotes a polynucleotide sequence that controls transcription of a gene/structural gene or nucleic acid sequence to which it is operably linked. A promoter nucleic acid includes signals for RNA polymerase binding and transcription initiation. The used promoter nucleic acid will be functional in the cell in which expression of the selected structural gene is contemplated. A large number of promoter nucleic acids including constitutive, inducible and repressible promoters from a variety of different sources are well known in the art (and identified in databases such as GenBank) and are available as or within cloned polynucleotides (from, e.g., depositories such as ATCC as well as other commercial or individual sources).

A "promoter nucleic acid" denotes a nucleotide sequence that directs or promotes the transcription of an operably linked structural gene. Typically, a promoter nucleic acid is located in the 5' non-coding or untranslated region of a gene, proximal to the transcriptional start site of the structural gene. Sequence elements within promoter nucleic acids that function in the initiation of transcription are often characterized by consensus nucleotide sequences. These elements include RNA polymerase binding sites, TATA sequences, CAAT sequences, differentiation-specific elements (DSEs), cyclic AMP response elements (CREs), serum response elements (SREs), glucocorticoid response elements (GREs), and binding sites for other transcription factors, such as CRE/ATF, AP2, SP1, cAMP response element binding protein (CREB) and octamer factors. If a promoter nucleic acid is an inducible promoter nucleic acid, then the rate of transcription increases in response to an inducing agent, such as a CMV promoter nucleic acid followed by two tet-operator site, the metallothionein and heat shock promoter nucleic acids. The rate of transcription is not regulated by an inducing agent if the promoter nucleic acid is a constitutively active promoter nucleic acid. Among the eukaryotic promoter nucleic acids that have been identified as strong promoter nucleic acids for expression are the SV40 early promoter nucleic acid, the adenovirus major late promoter nucleic acid, the mouse metallothionein-I promoter nucleic acid, the Rous sarcoma virus long terminal repeat, the Chinese hamster elongation factor 1 alpha (CHEF-1), human EF-1 alpha, ubiquitin, and human cytomegalovirus immediate early promoter nucleic acid (CMV IE).

The term "selection marker" denotes a nucleic acid that allows cells carrying it to be specifically selected for or against, in the presence of a corresponding selection agent. Typically, a selection marker will confer resistance to a drug or compensate for a metabolic or catabolic defect in the cell into which it is introduced. A selection marker can be positive, negative, or bifunctional. A useful positive selection marker is an antibiotic resistance gene allowing for the selection of cells transformed therewith in the presence of the corresponding selection agent, e.g. the antibiotic. A non-transformed cell is not capable to grow or survive under the selective conditions, i.e. in the presence of the selection agent. Negative selection markers allow cells carrying the marker to be selectively eliminated. Selection markers used with eukaryotic cells include, e.g., the structural genes encoding aminoglycoside phosphotransferase (APH), such as e.g. the hygromycin (hyg), neomycin (neo), and G418 selection markers, dihydrofolate reductase (DHFR), thymidine kinase (tk), glutamine synthetase (GS), asparagine synthetase, tryptophan synthetase (selection agent indole), histidinol dehydrogenase (selection agent histidinol D), and nucleic acids conferring resistance to puromycin, bleomycin, phleomycin, chloramphenicol, Zeocin, and mycophenolic acid.

The term "short-term production rate" denotes the amount of polypeptide produced by a single cell within one day as determined from the amount of polypeptide produced within a given time period and the viable cell density, wherein the time period is short. In one embodiment the short-term cultivation is for of from 2 to 20 days, in another embodiment for of from 4 to 15 days, and in still a further embodiment for of from 10 to 14 days.

The term "specific production rate" or "production rate" denotes the amount of polypeptide produced by a single cell within one day as determined from the amount of polypeptide produced within a given time period and the viable cell density. The specific production rate (SPR) can be calculated using the following formula:

$$SPR = P_2 - P_1/((D_2 - D_1)/2 * \Delta t) \quad \text{(Formula 2)}$$

with
SPR [pg/cell/d]: specific production rate,
$P_1$ [µg/ml]: polypeptide concentration at the beginning of the time period,
$P_2$ [µg/ml]: polypeptide concentration at the end of the time period,
$D_1$ [cells/ml]: viable cell density at the beginning of the time period,
$D_2$ [cells/ml]: viable cell density at the end of the time period,
$\Delta t$ [d]: duration of the time period.

The term "structural gene" denotes the region of a gene without a signal sequence, i.e. the coding region.

Cells producing a polypeptide, i.e. cells transfected with a nucleic acid comprising an expression cassette containing a structural gene encoding a heterologous polypeptide, can be grouped in different classes: In a first class of cells the specific production rate is almost constant over multiple generations whereas in the second class of cells the specific production rate is decreasing, especially monotonically decreasing, over multiple generations. The diminishing productivity of polypeptide producing cells and cell lines, respectively, is caused by the steadily increasing methylation and therewith silencing of the promoter nucleic acid operably linked to the structural gene encoding the polypeptide or by loss of copies of the structural gene.

It has been found that the presence of detectable methylation in the promoter nucleic acid that is operably linked to the structural gene encoding a polypeptide provides information regarding the long-term productivity of the cell or cell line, respectively.

Each promoter nucleic acid used for the expression of a structural gene comprises sites prone to methylation by the cell's enzymes into which it has been introduced if the promoter nucleic acid is not shielded by protective elements.

A site amenable to methylation is termed CpG-site and comprises/consists of the dinucleotide CG. But not all CpG-sites are methylated with the same relative frequency—some of the CpG-sites are methylated more often than others. It has been found that certain sites e.g. within the human CMV promoter are methylated with different frequency and have a different impact on promoter silencing.

The following method can be used for identifying a CpG-site in a nucleic acid sequence. It comprises the steps:
1) providing a cell with a production rate of a polypeptide that is after a cultivation time of 30 generations of the cell in the absence of a selection agent less than 90% of the production rate of the cell after the first generation of the cultivation,
2) separately isolating the DNA from at least 10 cells of a cultivation of the cell of 1),
3) modifying the cytosine of the isolated DNA by bisulfite treatment,
4) identifying a CpG site within the promoter nucleic acid operably linked to the structural gene encoding the polypeptide with a methylation frequency of at least 0.2 based on the DNA obtained in step 3) and thereby identifying a CpG-site.

In one embodiment the production rate of the cell after a cultivation time of 30 generations is 60% or less than the production rate of the cell after the first generation of the cultivation. In another embodiment the methylation frequency is at least 0.4. In a further embodiment the DNA is isolated from at least 20 cells. In also an embodiment the promoter nucleic acid has the sequence of SEQ ID NO: 01 or comprises a fragment thereof or a variant thereof.

In one embodiment the modifying the cytosine of the isolated DNA by bisulfite treatment comprises the following steps:
3-a) incubating the isolated DNA in the presence of sulfite ions whereby the DNA is deaminated, and
3-b) incubating the deaminated DNA under alkaline conditions whereby the deaminated DNA is desulfonated.

A method for obtaining a cell producing a polypeptide is a process comprising at least one transfecting step and at least one selecting step including single cell depositing of successfully transfected cells either directly after transfection or after growth in the presence of a selection agent. In the selecting step cells are identified based on their short-term specific production rate, i.e. based on the polypeptide concentration in the supernatant after a short-term cultivation. Among the selected cells some have a specific production rate that is almost constant over multiple generations and others have a specific production rate that is monotonously decreasing over multiple generations. Thus, with generally applied selection criteria no specific selection of a cell or cells with a stable long-term productivity can be made.

Thus, herein is reported a method for selecting a cell producing a polypeptide comprising the following steps:
a) determining for at least one cell comprising a nucleic acid comprising a structural gene encoding the polypeptide operably linked to a promoter nucleic acid the methylation of a CpG-site with high methylation frequency within the promoter nucleic acid, and
b) selecting a cell producing a polypeptide wherein the methylation determined in step b) is below a threshold value.

In the method as reported herein any cell obtained by transfection with an expression plasmid comprising an expression cassette comprising a promoter nucleic acid operably linked to a structural gene encoding a polypeptide of interest to be produced by the transfected cell can be analyzed. The expression plasmid generally comprises also a selection marker. Thus, in one embodiment the cells are cultivated in the presence of a selection agent after the transfecting step and prior to the selecting step. In another embodiment the method comprises cultivating the cells without prior single cell deposition or limited dilution as pool in the presence of a selection agent. In a further embodiment the method comprises cultivating the cells after single cell deposition or limiting dilution.

In one embodiment the determining comprises
1) individually isolating the DNA from each of the provided cells,
2) performing a methylation specific PCR,
3) calculating with the results obtained in step 2) the methylation of a CpG site with high methylation frequency within the promoter nucleic acid.

In another embodiment step 2) is
1) performing a PCR with a methylation specific primer and a universal primer, or
2) digesting the DNA with a restriction enzyme and performing a PCR with the digested DNA and a methylation specific primer and a universal primer.

After the pool cultivation/selection a single cell deposition has to be performed. If the single cell deposition is performed after a pool cultivation step the cells are also further cultivated after the single cell deposition.

In order to identify cells or cell lines with a specific production rate that is almost constant over multiple generations the polypeptide concentration in the supernatant and the viable cell density have to be determined at defined cultivation times in a long-term cultivation over multiple generations. A CpG-site with a high methylation frequency can be identified by bisulfite treatment of single stranded DNA, e.g. at pH 5, with succeeding alkaline desulfurization. Herein methylated and non-methylated CpG-sites can be discriminated. Under the specific treatment conditions cytosine but not 5-methyl-cytosine is deaminated at position 4 of the N-heterocycle and converted to uracil. Complementary DNA strands are converted into two strands, strand A and strand B, which are no longer complementary. The determination can be based on any of these strands.

This long-term cultivation has to be performed only once for the promoter nucleic acid or combination of promoter nucleic acid and cell line. If the same promoter nucleic acid or combination is used a second time the selection can be based on the already collected data.

A number of techniques can be applied to reveal sequence differences between methylated and non-methylated alleles after bisulfite treatment. In one embodiment the sequence of interest (either strand A or strand B) can be amplified by PCR under non-methylation specific conditions, i.e. with primer not sensitive to methylated sites, and subsequently analyzed by methods such as DNA sequencing (with or without cloning), high resolution melting point analysis or microarray analysis. In another embodiment a quantitative PCR (qPCR) with methylation sensitive or methylation specific primer or probes can be performed. In an alternative embodiment methylated DNA is precipitated with 5-methyl cytosine specific antibodies followed by a quantitative polymerase chain reaction.

Methylation specific PCR (MSP) can also be used to address the sequence of bisulfite treated DNA directly without previous PCR amplification of the region of interest. Primers used in MSP shall comprise one or more CpG-sites. They are either complementary to unconverted 5-methylcytosine for the detection of methylated DNA or complementary to uracil converted from cytosine for the detection of non-methylated DNA.

The methylation of the identified CpG-sites is determined for a number of cells. In one embodiment the number of cells is at least 10, in another embodiment at least 15, and in a further embodiment at least 20. Afterwards the methylation frequency for each CpG-site is calculated, i.e. for each CpG-site the number of cells methylated at that CpG-site divided by the total number of cells analyzed is calculated. The determination of the methylation frequency is done for a cell or for a number of cells that show the highest decrease in the specific production rate during long-term cultivation. In one embodiment a CpG-site with a high methylation frequency is a CpG-site that has a methylation frequency of at least 0.2, in another embodiment of at least 0.25, in a further embodiment of at least 0.4, and in still a further embodiment of at least 0.5.

After the determination of CpG-sites with a high methylation frequency the methylation of the respective CpG-sites in a number of cells that have shown the lowest or almost no decrease in the specific production rate during long-term cultivation is carried out.

A CpG-site with high methylation frequency suitable for the method as reported herein is a CpG-site that has a high methylation frequency determined based on a number of cells that show a decrease in the specific production rate during long-term cultivation and that has a methylation frequency determined based on a number of cells that show the lowest or almost no decrease in the specific production rate during the long-term cultivation which is below a predetermined threshold value.

In one embodiment the predetermined threshold value is five times the average value of apparent methylation of a cytosine at a non-CpG-site. The term "apparent" denotes that although no methylation is present a frequency of methylation can be determined. Thus, this value corresponds to the background noise. In another embodiment the threshold value is three times the average. In a further embodiment the threshold value is two-times the average value. The same threshold values can be used in the selecting step of the method as reported herein.

Another aspect as reported herein is a method for the production of a polypeptide comprising the following steps:
a) selecting a cell producing a polypeptide according to the aspect as reported herein,
b) cultivating the selected cell, and
c) recovering the polypeptide from the cultivation medium and/or the cell and thereby producing a polypeptide.

In one embodiment the method comprises a further step
d) purifying the recovered polypeptide.

In another embodiment the method comprises prior to step a) the following steps:
a-3) providing a cell,
a-2) transfecting the provided cell with a nucleic acid containing a structural gene encoding the polypeptide operably linked to a promoter nucleic acid,
a-1) i) optionally cultivating the transfected cell in the presence of a selection agent, ii) single depositing the transfected cells, and iii) cultivating the single deposited transfected cells in the presence of a selection agent.

In one embodiment step a) comprises:
i) providing at least one cell comprising a nucleic acid comprising a structural gene encoding the polypeptide operably linked to a promoter nucleic acid,
ii) determining the methylation of a CpG-site with high methylation frequency within the promoter nucleic acid, and
iii) selecting a cell producing a polypeptide wherein the methylation determined in step b) is below a threshold value.

It has been found that even low levels of methylated promoter nucleic acid, i.e. above a predetermined threshold value, in a cell or cell line used for the production of a polypeptide can be used to predict a decrease in productivity during long-term cultivation.

Thus, an aspect as reported herein is a method for determining methylation of a promoter nucleic acid operably linked to a nucleic acid encoding a, optionally heterologous, polypeptide and thereby determining the long-term productivity of the cell. Also an aspect is a method for selecting a cell for producing a polypeptide by determining the methylation of the promoter nucleic acid operably linked to the structural gene encoding the polypeptide.

In more detail the method comprises in one embodiment the following steps:
a) providing a cell with stable long-term productivity and a cell with non-stable long-term productivity,
b) identification of methylated CpG sites by cloning bisulfite treated promoter nucleic acid from the cell line with non-stable long-term productivity by using the promoter nucleic acid from the cell line with stable long-term productivity as reference,
c) optionally performing a high-resolution melting point analysis,
d) providing methylation sensitive PCR primer or probes for the methylated CpG site identified in step b),
e) optionally verifying the predictive value of the identified methylated CpG site by providing further cell lines with stable and non-stable long-term productivity.

In one embodiment step e) is performed with at least 10 different cells or cell lines derived from the same parent cell line and comprising the same expression cassette for expressing a polypeptide of interest operably linked to the same promoter nucleic acid.

In one embodiment the DNA is digested prior to the bisulfite treatment.

In one embodiment the cell is a eukaryotic cell. In another embodiment the cell is a mammalian cell. In a further embodiment the cell is selected from CHO cell, BHK cell, HEK cell, and Sp2/0 cell. In still another embodiment the cell is a CHO cell. In a further embodiment the cell is a CHO K1 cell.

In FIG. 1 the number of methylated CpG site of the same promoter nucleic acid obtained from different cells is shown.

The methods as reported herein are in the following exemplified with the human cytomegalovirus immediate early promoter (CMV IE promoter) which was available in sufficient quantities in our laboratories at the time the invention was made. This data is presented in order to exemplify the methods as reported herein and not as limitation. The scope of the invention is set forth in the claims.

The human CMV IE promoter as a nucleic acid sequence as depicted in the following (CpG sites are underlined):

```
ATGTTGACATTGATTATTGACTAGTTATTAATAGTAATCAATTACGGGGT

CATTAGTTCATAGCCCATATATGGAGTTCCGCGTTACATAACTTACGGTA

AATGGCCCGCCTGGCTGACCGCCCAACGACCCCCGCCCATTGACGTCAAT
```

AATGA<u>CG</u>TATGTTCCCATAGTAA<u>CG</u>CCAATAGGGACTTTCCATTGA<u>CG</u>TC

AATGGGTGGAGTATTTA<u>CG</u>GTAAACTGCCCACTTGGCAGTACATCAAGTG

TATCATATGCCAAGTA<u>CG</u>CCCCCTATTGA<u>CG</u>TCAATGA<u>CG</u>GTAAATGGCC

<u>CG</u>CCTGGCATTATGCCCAGTACATGACCTTATGGGACTTTCCTACTTGGC

AGTACATCTA<u>CG</u>TATTAGTCAT<u>CG</u>CTATTAGCATGGTGAT<u>GCG</u>GTTTTGG

CAGTACATCAATGGG<u>CG</u>TGGATAG<u>CG</u>TTTGACTCA<u>CG</u>GGGATTTCCAAG

TCTCCACCCCATTGA<u>CG</u>TCAATGGGAGTTTGTTTTGGCACCAAAATCAA<u>C</u>

GGGACTTTCCAAAATGT<u>CG</u>TAACAACTC<u>CG</u>CCCCATTGA<u>CG</u>CAAATGGG<u>C</u>

GGTAGG<u>CG</u>TGTA<u>CG</u>GTGGGAGGTCTATATAAGCAGAGCTC<u>CG</u>TTTAGTGA

A<u>CG</u>

(SEQ ID NO: 01).

In SEQ ID NO: 01 thirty-three CpG sites are present, which are potential sites for nucleic acid methylation. With the method as outlined above cytosine residues within the human CMV promoter that are predominantly methylated can be identified.

The strand A with all CpG-sites preserved has the nucleotide sequence

ATGTTGATATTGATTATTGATTAGTTATTAATAGTAATTAATTA<u>CG</u>GGGT

TATTAGTTTATAGTTTATATATGGAGTTT<u>CGCG</u>TTATATAATTTA<u>CG</u>GTA

AATGGTT<u>CG</u>TTTGGTTGAT<u>CG</u>TTTAA<u>CG</u>ATTTT<u>CG</u>TTTATTGA<u>CG</u>TTAAT

AATGA<u>CG</u>TATGTTTTATAGTAA<u>CG</u>TTAATAGGGATTTTTTATTGA<u>CG</u>TT

AATGGGTGGAGTATTTA<u>CG</u>GTAAATTGTTTATTTGGTAGTATATTAAGTG

TATTATATGTTAAGTA<u>CG</u>TTTTTTATTGA<u>CG</u>TTAATGA<u>CG</u>GTAAATGGTT

<u>CG</u>TTTGGTATTATGTTTAGTATATGATTTTATGGGATTTTTTATTTGGT

AGTATATTTA<u>CG</u>TATTAGTTAT<u>CG</u>TTATTAGTATGGTGAT<u>GCG</u>GTTTTGG

TAGTATATTAATGGG<u>CG</u>TGGATAG<u>CG</u>TTTGATTTA<u>CG</u>GGGATTTTTAAG

TTTTTATTTTATTGA<u>CG</u>TTAATGGGAGTTTGTTTTGGTATTAAAATTAA<u>C</u>

GGGATTTTTTAAAATGTCGTAATAATTT<u>CG</u>TTTTATTGA<u>CG</u>TAAATGGG<u>C</u>

GGTAGG<u>CG</u>TGTA<u>CG</u>GTGGGAGGTTTATATAAGTAGAGTTT<u>CG</u>TTTAGTGA

A<u>CG</u>

(SEQ ID NO: 02) and the completely deaminated strand A has the nucleotide sequence ATGTTGATATTGATTATTGATTAGTTATTAATAGTAATTAATTA<u>TG</u>GGGT TATTAGTTTATAGTTTATATATGGAGTTT<u>TGTG</u>TTATATAATTTA<u>TG</u>GTA AATGGTT<u>TG</u>TTTGGTTGAT<u>TG</u>TTTAA<u>TG</u>ATTTT<u>TG</u>TTTATTGA<u>TG</u>TTAAT AATGA<u>TG</u>TATGTTTTATAGTAA<u>TG</u>TTAATAGGGATTTTTTATTGA<u>TG</u>TT AATGGGTGGAGTATTTA<u>TG</u>GTAAATTGTTTATTTGGTAGTATATTAAGTG TATTATATGTTAAGTA<u>TG</u>TTTTTTATTGA<u>TG</u>TTAATGA<u>TG</u>GTAAATGGTT <u>TG</u>TTTGGTATTATGTTTAGTATATGATTTTATGGGATTTTTTATTTGGT AGTATATTTA<u>TG</u>TATTAGTTATT<u>GT</u>TATTAGTATGGTGAT<u>GTG</u>GTTTTGG TAGTATATTAATGGG<u>TG</u>TGGATAG<u>TG</u>TTTGATTTA<u>TG</u>GGGATTTTTAAG TTTTTATTTTATTGA<u>TG</u>TTAATGGGAGTTTGTTTTGGTATTAAAATTAA<u>T</u>

GGGATTTTTTAAAATGT<u>TG</u>TAATAATTTT<u>GT</u>TTTATTGA<u>TG</u>TAAATGGG<u>T</u>

GGTAGG<u>TG</u>TGTA<u>TG</u>GTGGGAGGTTTATATAAGTAGAGTTT<u>TG</u>TTTAGTGA

ATG (SEQ ID NO: 03). The strand B with all CpG-sites preserved has the nucleotide sequence

CGTTTATTAAACGGAGTTTTGTTTATATAGATTTTTTATCGTATACGTTT

ATCGTTTATTTGCGTTAATGGGGCGGAGTTGTTACGATATTTTGGAAAGT

TTCGTTGATTTTGGTGTTAAAATAAATTTTTATTGACGTTAATGGGGTGG

AGATTTGGAAATTTTCGTGAGTTAAATCGTTATTTACGTTTATTGATGTA

TTGTTAAAATCGTATTATTATGTTAATAGCGATGATTAATACGTAGATGT

ATTGTTAAGTAGGAAAGTTTTATAAGGTTATGTATTGGGTATAATGTTAG

GCGGGTTATTTATCGTTATTGACGTTAATAGGGGCGTATTTGGTATATG

ATATATTTGATGTATTGTTAAGTGGGTAGTTTATCGTAAATATTTTATTT

ATTGACGTTAATGGAAAGTTTTTATTGGCGTTATTATGGGAATATACGTT

ATTATTGACGTTAATGGGCGGGGGTCGTTGGGCGGTTAGTTAGGCGGGTT

ATTTATCGTAAGTTATGTAACGCGGAATTTTATATATGGGTTATGAATTA

ATGATTTCGTAATTGATTATTATTAATAATTAGTTAATAATTAATGTTAA

TAT (SEQ ID NO: 04) and strand B in completely deaminated form has the nucleotide sequence

TGTTTATTAAATGGAGTTTTGTTTATATAGATTTTTTATTGTATATGTTT

ATTGTTTATTTGTGTTAATGGGGTGGAGTTGTTATGATATTTTGGAAAGT

TTTGTTGATTTTGGTGTTAAAATAAATTTTTATTGATGTTAATGGGGTGG

AGATTTGGAAATTTTTGTGAGTTAAATTGTTATTTATGTTTATTGATGTA

TTGTTAAAATTGTATTATTATGTTAATAGTGATGATTAATATGTAGATGT

ATTGTTAAGTAGGAAAGTTTTATAAGGTTATGTATTGGGTATAATGTTAG

GTGGGTTATTTATTGTTATTGATGTTAATAGGGGTGTATTTGGTATATG

ATATATTTGATGTATTGTTAAGTGGGTAGTTTATTGTAAATATTTTATTT

ATTGATGTTAATGGAAAGTTTTTATTGGTGTTATTATGGGAATATATGTT

ATTATTGATGTTAATGGGTGGGGGTTGTTGGGTGGTTAGTTAGGTGGGTT

ATTTATTGTAAGTTATGTAATGTGGAATTTTATATATGGGTTATGAATTA

ATGATTTTGTAATTGATTATTATTAATAATTAGTTAATAATTAATGTTAA

TAT (SEQ ID NO: 05).

In FIGS. 4A-E the frequency of methylation at individual CpG-sites in different cell lines is shown. The numbers have been determined by analyzing 19 to 22 different clones obtained from different CHO parent cell lines after transfection with a plasmid comprising an expression cassette for expressing a polypeptide. It shows the methylation patterns of single DNAs (bottom) and the frequency of methylation at single CpG sites (top) for each cell line. Cell line K18.1 is highly methylated (FIG. 4A). The frequency of methylation is not equal at the different CpG sites but seems to have centers in 3 clusters, i.e. at the 5'-end, the 3'-end and at around position (or nucleotide, respectively,) 400. Fourteen out of 22 sequenced inserts sequenced had a cytosine at position 425. The methylation of the promoter nucleic acid in cell line 43-16 A10 is shown in FIG. 4E. The distribution of methylation is similar to the distribution observed with cell line K18.1. As with K18.1 the position 425 was methylated most often—five of 20 inserts sequenced contained a cytosine in this position.

In three other analyzed cell lines cytosine is detected sporadically, i.e. as single events, at different CpG sites (FIGS. 4B, 4C and 4D). To obtain statistic significance for cell lines with a low overall methylation sequencing of hundreds of inserts would be required. Additionally the single events may also represent false positive events due to incomplete cytosine deamination rather than actual promoter methylation.

For reliable determination of CpG position specific methylation a methylation specific PCR method has been developed. For the methylation specific PCR primers as shown in the following Table can be used. These primer either alone or in combination are also aspects as reported herein.

TABLE

Primers that can be used in methylation specific PCR.

| primer no. (direction) | methylation specific | nucleotide sequence | SEQ ID NO: |
|---|---|---|---|
| 227 (forward) | no | ATGTTGATATTGATTATTGATTAG | 06 |
| 228 (forward) | no | TATGGGATTTTTTATTTGGTAGT | 07 |
| 229 (reverse) | no | ACTCCTCTCCCAAAACTAAATCTA | 08 |
| 237 (reverse) | no | CCAAAACAAACTCCCATTAAC | 09 |
| 238 (forward) | no | GGGGTTATTAGTTTATAGTTTATA | 10 |
| 239 (forward) | no | TGGTATTATGTTTAGTATATGATTTTAT | 11 |
| 240 (forward) | no | GGATTTTTTATTTGGTAGTATATT | 12 |
| 254 (reverse) | yes | AAATCCCCGTAAATCAAACCG | 13 |
| 263 (forward) | no | GGGATTTTTTATTTGGTAGTATATT | 14 |
| 264 (forward) | no | TATGGGATTTTTTATTTGGTAGTA | 15 |
| 265 (reverse) | yes | ATCCCCGTAAATCAAACCG | 16 |
| 266 (reverse) | yes | TCCCCGTAAATCAAACCG | 17 |
| 267 (reverse) | yes | CCCCGTAAATCAAACCG | 18 |
| 268 (reverse) | yes | CCCGTAAATCAAACCGC | 19 |

TABLE -continued

Primers that can be used in methylation specific PCR.

| primer no. (direction) | methylation specific | nucleotide sequence | SEQ ID NO: |
|---|---|---|---|
| 262 (reverse) | yes | AAATCCCCRTAAATCAAACCG | 20 |

In the course of primer evaluation it has been found that methylation specific primer pairs, that are highly selective for deaminated CMV promoter DNA with a cytosine at position 425, differ in their properties (see FIG. 6). In one embodiment the primer for the methylation specific PCR have the nucleotide sequence of SEQ ID NO: 14 and SEQ ID NO: 18.

Thus, in one embodiment of the methods as reported herein is the promoter nucleic acid the human CMV promoter nucleic acid of SEQ ID NO: 01. In one embodiment the CpG-site with high methylation frequency is selected from the CpG-sites at position (bp) 80, 96, 425, 437, 563 and 591 of SEQ ID NO: 01. In another embodiment the CpG-site with high methylation frequency is selected from the CpG-site at position (bp) 425 and combinations of the CpG-site at position (bp) 425 with at least one of the CpG-sites at position (bp) 80, 96, 438, 563 and 591.

TABLE

Expected results for methylation specific (MSP) primer pairs and universal primer pair in qPCR.

| | Template | | | |
|---|---|---|---|---|
| | #11 | #62 | #01 | #04 |
| position 425 | T | C | C | T |
| position 437 | T | C | T | C |
| | Amplification | | | |
| methylation specific primer pair | − | + | + | − |
| universal primer pair | + | + | + | + |

The universal primer pair should amplify all four templates whereas the MSP primer pair should selectively amplify template #62 (SEQ ID NO: 22) and template #01 (SEQ ID NO: 23). The ΔCp value should be as small as possible between the MSP primer pair and the universal primer pair on template #62 and template #01. By contrast, Cp values obtained with the MSP primer pair on templates #11 (SEQ ID NO: 21) and #04 (SEQ ID NO: 24) should be as high as possible, i.e. ΔCp compared to amplification with the universal primer pair should be maximal.

The methylation specific primer should be able to detect 5-methyl cytosine at position 425 selectively albeit two further methylation positions are present at position 416 and 437.

The determination of the methylation is possible with a frequency of methylation of from 1% to 100%.

Comparable results with respect to the methylation extent were observed with a methylation specific PCR and by cloning and sequencing, but the methylation specific PCR is much more sensitive. Cell lines with a decreasing productivity in long-term production have a methylation at position 425 with a methylation frequency above a threshold value. The threshold value is in one embodiment twice the background noise of the determination method. A cell line with long-term stable productivity has a frequency of methylation at the CpG site that is below the threshold value.

For high-resolution melting point analysis the promoter nucleic acid is amplified starting from position 334 up to position 487, i.e. 154 bp. An exemplary melting point analysis is shown in FIG. 10A and its first derivative in FIG. 10B. It can be seen that with a high-resolution melting point analysis a methylated promoter nucleic acid (template #16, SEQ ID NO: 25) can be distinguished from a non-methylated promoter nucleic acid (template #11). The methylated promoter nucleic acid fragment can be detected at a relative frequency of 50% or more. The non-methylated promoter fragment can be detected at a relative frequency of 10% or more.

These data show that the stability of recombinant CHO cell lines that contain foreign genes driven by the human CMV immediate-early promoter/enhancer can be predicted by measuring the methylation status of the cytosine at position 425.

Thus, it has been found that the determination of C425 methylation can be used as a predictive marker to determine the stability of polypeptide expression in generated cell clones and thereby allowing the selection of stable clones with stable productivity during cell line development. It has further been found that C425 methylation of 5% or less is a suitable criterion for the selection of stable cell clones. It has also been found that the fraction of cell clones that are falsely predicted as stable (false negative cell clones) can be reduced by cultivating them for some time in the absence of MTX before testing.

Having established a sensitive and accurate PCR method to quantify methylation of hCMV-MIE nucleotide at CpG site 425, the methylation in recombinant CHO cell lines K18.1, 43 16 A10 and G45-2 has been assessed. The bisulfite-treated DNA that had been analyzed by sequencing was used as template in methylation-specific real time qPCR, either directly or after PCR amplification of the complete hCMV-MIE region (FIGS. 8A and 8B). The two assay set-ups provided comparable results. More importantly, they correlated well with the results of bisulfite sequencing. This demonstrates that the CpG site 425 methylation-specific qPCR assay can be used to measure hCMV-MIE methylation at CpG site 425 in recombinant CHO cell lines and can be used without previous PCR amplification of the target DNA.

In principal, other CpG sites within the CMV immediate-early promoter/enhancer DNA could be explored to predict production instability. However, methylation at C425 was found to be approximately 5-fold higher than the average methylation at all CpG sites. Moreover some sites were not methylated at all even in highly methylated cell clones, e.g. C280 and C289 (FIGS. 4C, 4E and 13). By chosen the right i.e. frequently modified CpG site for promoter methylation analysis the assay becomes more sensitive. Significant methylation of clones G25-17, G25-10 and 43-16 A10 which is about 10% would likely be missed, if a CpG site was randomly chosen for analysis.

The stability prediction by addressing the methylation status of a relevant CpG sites within a promoter nucleic acid can be used also with other heterogenic promoter nucleic acids.

To evaluate a potential correlation of early promoter methylation and production instability, CpG site 425 methylation at the start of the stability study was plotted against the relative alteration of qP in the presence or in the absence of MTX. The correlation plots are shown in FIG. 11A (with MTX) and FIG. 11B (without MTX). For the evaluation, the plot areas were divided into four compartments with limits at 5% methylation—equaling the two to three-fold background of the methylation measurement, i.e. the limit of detection—and 40% decrease in qP—representing the acceptance limit of production stability. The number of clones in the different compartments was determined. Contingency analysis of stability status by methylation status using a Pearson chi square test demonstrated a significant association with a p-value of 0.05 for cultivation with MTX and a trend with a p-value of 0.13 for cultivation without MTX. It turned out that the majority of clones with less than 5% methylation at CpG site 425 were found in the fraction of stable clones (less than 40% decrease in qP with or without MTX, shown in upper left compartments).

Thus, summarizing the above, loss of productivity during scale-up is a major risk in the development of manufacturing cell lines. Therefore, there exists a need for molecular markers of production instability that can be rapidly and easily examined. It has been found that promoter methylation can be employed to predict a future loss of productivity in recombinant CHO cell lines. To assess this, DNA methylation of 33 CpG sites within a 603 bp region of the widely used hCMV-MIE promoter/enhancer was analyzed. The overall methylation level of the region investigated varied between approximately 1% and 18% of all CpG sites. 1% apparent methylation represents the technical background that results from incomplete deamination of non-methylated cytosines (data not shown). Moreover, within methylated promoters, the level of methylation greatly varies between individual CpG sites and accumulates in three clusters with a maximum at CpG site 425. Methylation at site CpG 425 appeared to be approximately 5-fold higher than the average degree of methylation of all other CpG sites. On the other hand, some CpG sites appear to be completely non-methylated, even in highly methylated cell lines. The overall methylation of hCMV-MIE, as well as the distribution of methylation between individual CpG sites, can vary considerably between cell types and tissues (see e.g. Kong, Q., et al., PLoS One 4 (2009) e6679, Krishnan, M., et al., FASEB J. 20 (2006) 106-108, Mehta, A. K., et al., Gene 428 (2009) 20-24 9).

It has been found that the dominant methylation of CpG site 425 is suited as marker for methylation of hCMV-MIE. It has been established a CpG site 425 methylation-specific qPCR as a fast and sensitive method with medium throughput. When analyzing a large number of cell lines by CpG site 425 methylation-specific qPCR, it has been found that the majority of unstable producers displayed more than 5% methylation at CpG site 425, even before long-term cultivation, whereas the majority of the stable producers showed less than 5% methylation at this site.

Early methylation of CpG site 425 was exclusively found with clones carrying more than ten copies of the heterologous plasmid. Previous reports have provided some evidence that tandem repeats of multiple transgene copies are more susceptible to methylation and silencing in mammalian cells (Garrick, D., et al., Nat. Genet. 18 (1998) 56-59, McBurney, M. W., et al., Exp Cell Res 274 (2002) 1-8).

Light chain gene copy numbers and methylation levels, both before stability testing, are plotted against each other in FIG. 15A. Early methylation, i.e. methylation before stability testing, was exclusively found with cells carrying more than ten transgene copies (black circles in FIG. 15A). As a consequence, selecting clones with low transgene copy numbers before stability testing likewise enriches clones with stable productivity. Two clones with ten or fewer than ten transgene copies acquired methylation during long-term cultivation (grey circles in FIG. 15A) copy numbers, from ten copies to three copies and from two copies to six copies.

Transgene copy numbers before and after long-term cultivation without MTX are compared in FIGS. 15A and 15B. In FIG. 15A CpG site 425 methylation of single clones at the start of stability testing (mCpG 425_start) plotted against the light chain gene copy number at the start of stability testing (LC gene copies_start); white circles: clones with CpG site 425 methylation below 5% at the beginning as well as at the end of long term stability testing; grey circles: clones rising above 5% in CpG site 425 methylation during long term stability testing; black circles: clones with CpG site 425 methylation above 5% at the beginning and at the end of stability testing. Clones are identified by numbers. In FIG. 15B light chain gene copy numbers (LC gene copies) of single clones at the start (S) of stability testing and at the end (E) of long-term cultivation without MTX is shown. White bars: clones with CpG site 425 methylation below 5% at the beginning as well as at the end of long-term stability testing; grey bars: clones rising above 5% in CpG site 425 methylation during long-term stability testing; black bars: clones with CpG site 425 methylation above 5% at the beginning and at the end of stability testing. Data represent mean values±SEM (error bars) of four independent experiments.

It has been shown herein that stable producers can be enriched by selecting clones with few transgene copies.

In summary, methylation of hCMV-MIE at CpG site 425 and high transgene copy numbers, i.e. the presence of more than 10 copies of the structural gene and the promoter nucleic acid, can be used as early indicators of production instability of recombinant CHO cell lines. These indicators provide an opportunity to enrich stable producers early in cell line development.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO: 01—Nucleotide sequence of the human CMV immediate early (hCMV) promoter/enhancer.
SEQ ID NO: 02—Nucleotide sequence of strand A of the hCMV promoter/enhancer, all CpG-sites preserved
SEQ ID NO: 03—Nucleotide sequence of strand A of the hCMV promoter/enhancer, completely deaminated
SEQ ID NO: 04—Nucleotide sequence of strand B of the hCMV promoter/enhancer, all CpG-site preserved
SEQ ID NO: 05—Nucleotide sequence of the completely deaminated strand B of the hCMV promoter/enhancer, completely deaminated
SEQ ID NO: 06—Primer 227.
SEQ ID NO: 07—Primer 228.
SEQ ID NO: 08—Primer 229.
SEQ ID NO: 09—Primer 237.
SEQ ID NO: 10—Primer 238.
SEQ ID NO: 11—Primer 239.
SEQ ID NO: 12—Primer 240.
SEQ ID NO: 13—Methylation specific primer 254.
SEQ ID NO: 14—Primer 263.
SEQ ID NO: 15—Primer 264.
SEQ ID NO: 16—Methylation specific primer 265.
SEQ ID NO: 17—Methylation specific primer 266.
SEQ ID NO: 18—Methylation specific primer 267.
SEQ ID NO: 19—Methylation specific primer 268.
SEQ ID NO: 20—Methylation specific primer 262
SEQ ID NO: 21—Sequence of template #11.
SEQ ID NO: 22—Sequence of template #62.
SEQ ID NO: 23—Sequence of template #01.
SEQ ID NO: 24—Sequence of template #04.
SEQ ID NO: 25—Sequence of template #16.
SEQ ID NO: 26—Primer 133.
SEQ ID NO: 27—Primer 132.
SEQ ID NO: 28—Primer 166.
SEQ ID NO: 29—Primer 178.
SEQ ID NO: 30—Primer 180.
SEQ ID NO: 31—Primer 185.

DESCRIPTION OF THE FIGURES

FIG. 3B: Specific production rate in the absence of a selection agent of cell line G25-10 over multiple generations in a long-term production.

FIG. 3C: Specific production rate in the absence of a selection agent of cell line G25-17 over multiple generations in a long-term production.

FIG. 3D: Specific production rate in the absence of a selection agent of cell line G42-5 over multiple generations in a long-term production.

FIG. 3E: Specific production rate in the absence of a selection agent of cell line 43-16 A10 over multiple generations in a long-term production.

FIG. 4A: cell line K18.1-methylation of all CpG sites: 12%, methylation of site C425: 64%, methylation of site C591: 27%, methylation of site C96: 32%;

FIG. 4B: cell line G25-10-methylation of all CpG sites: 0.5%, methylation of site C425: 0%, methylation of site C591: 5%, methylation of site C96: 0%;

FIG. 4C: cell line G25-17-methylation of all CpG sites: 0.3%, methylation of site C425: 0%, methylation of site C591: 0%, methylation of site C96: 0%;

FIG. 4D: cell line G42-5-methylation of all CpG sites: 0.6%, methylation of site C425: 0%, methylation of site C591: 0%, methylation of site C96: 0%;

FIG. 4E: cell line 43-16 A10-methylation of all CpG sites: 4.4%, methylation of site C425: 25%, methylation of site C591: 15%, methylation of site C96: 10%.

EXAMPLE 1

General Techniques

Recombinant DNA Techniques

Standard methods were used to manipulate DNA as described in Sambrook et al., Molecular Cloning: A Laboratory Manual, Second Edition, Cold Spring Harbor Laboratory Press, Cold Spring Harbor, N.Y. (1989). The molecular biological reagents were used according to the manufacturer's instructions.

DNA Sequence Determination

DNA sequencing was performed at SequiServe GmbH (Vaterstetten, Germany).

DNA and Protein Sequence Analysis and Sequence Data Management

The EMBOSS (European Molecular Biology Open Software Suite) software package and Invitrogen's Vector NTI version 9.1 were used for sequence creation, mapping, analysis, annotation and illustration.

Protein Determination

A chromatographic method was used to quantify the amount of antibody present in a sample. A PorosA column was used that binds the Fc-region of the antibody. The antibody binds to the column and is subsequently eluted by low pH conditions. Protein concentration was determined by determining the optical density (OD) at 280 nm, with a reference wavelength of 320 nm, using the molar extinction coefficient calculated on the basis of the amino acid sequence.

EXAMPLE 2

Generation of Recombinant CHO Cell Lines

Figure 1:
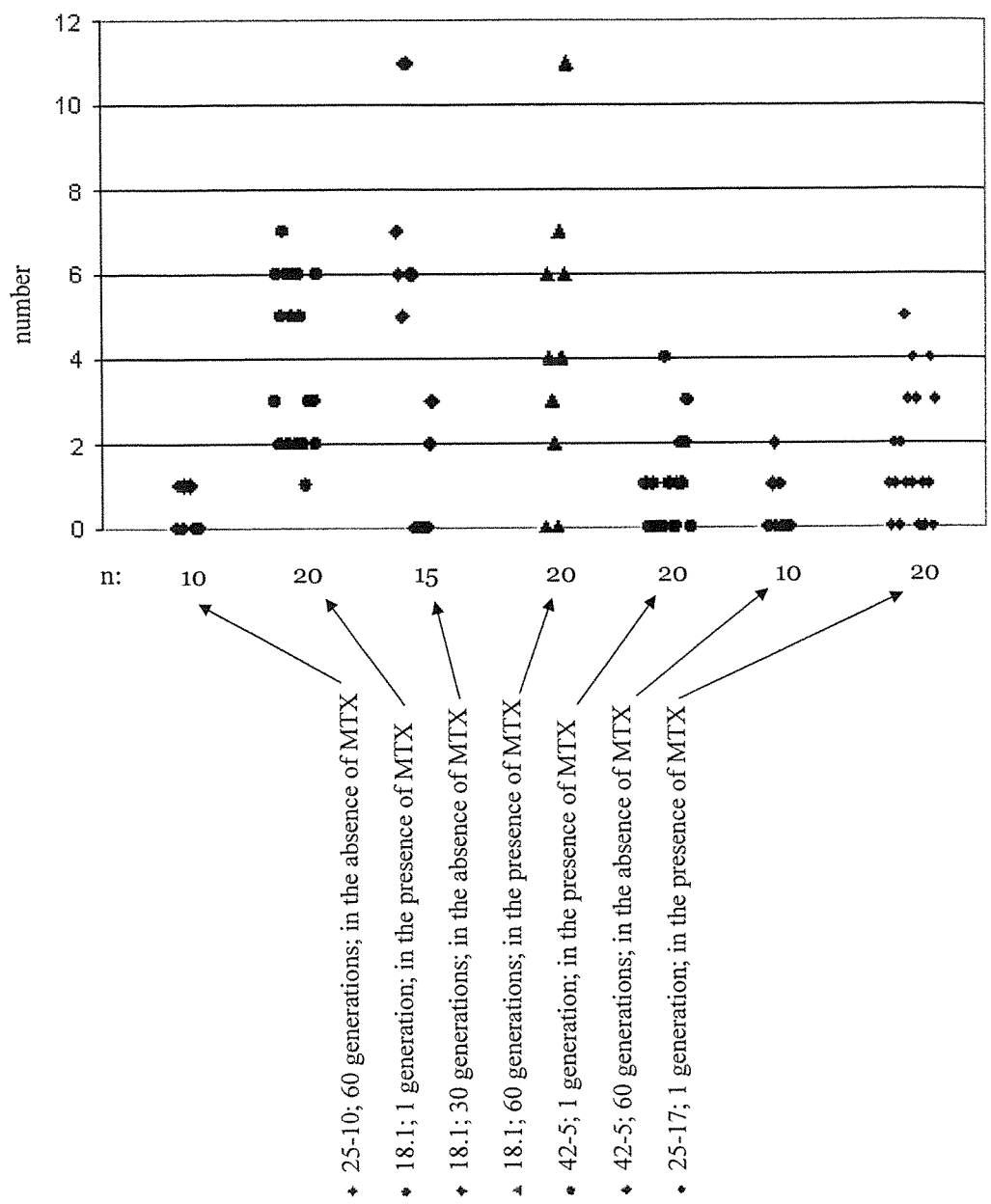
FIG. 1 Number of methylated CpG site of the hCMV promoter/enhancer obtained from different cell lines.
Figure 2:
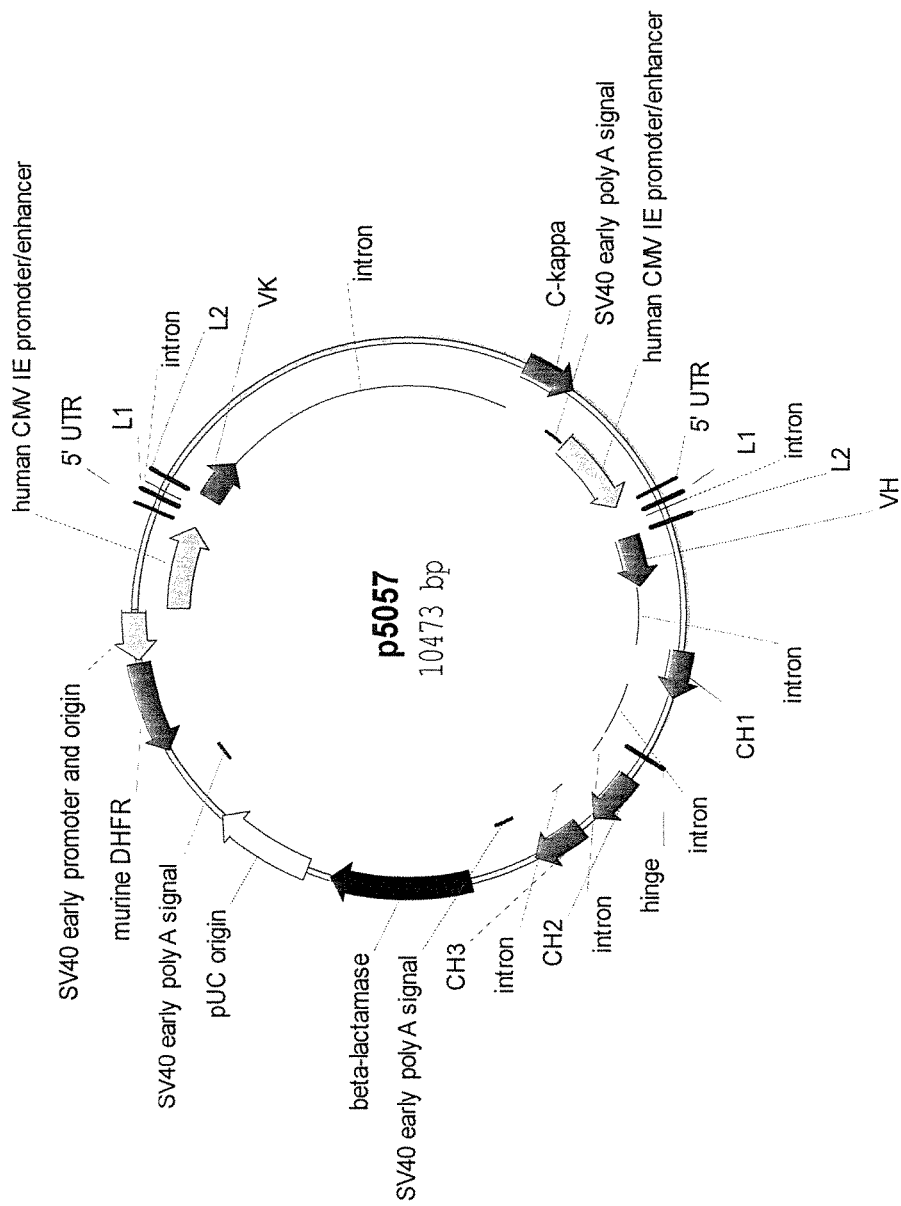
FIG. 2 Plasmid map of p5057.
Figure 3A:
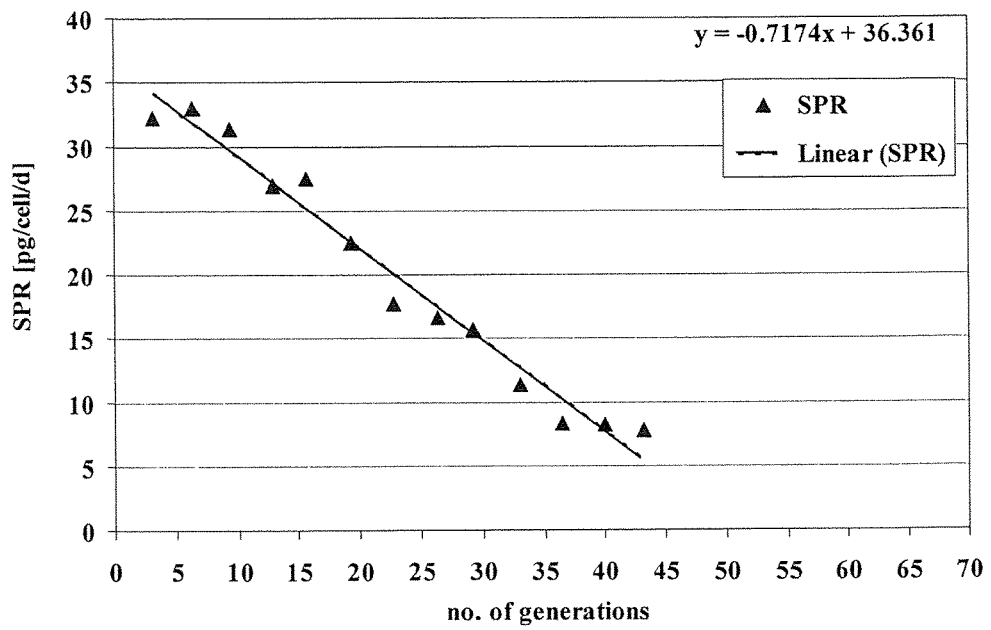
FIGS. 3A-E FIG. 3A: Specific production rate in the absence of a selection agent of cell line K18.1 over multiple generations in a long-term production.
Figure 3B:
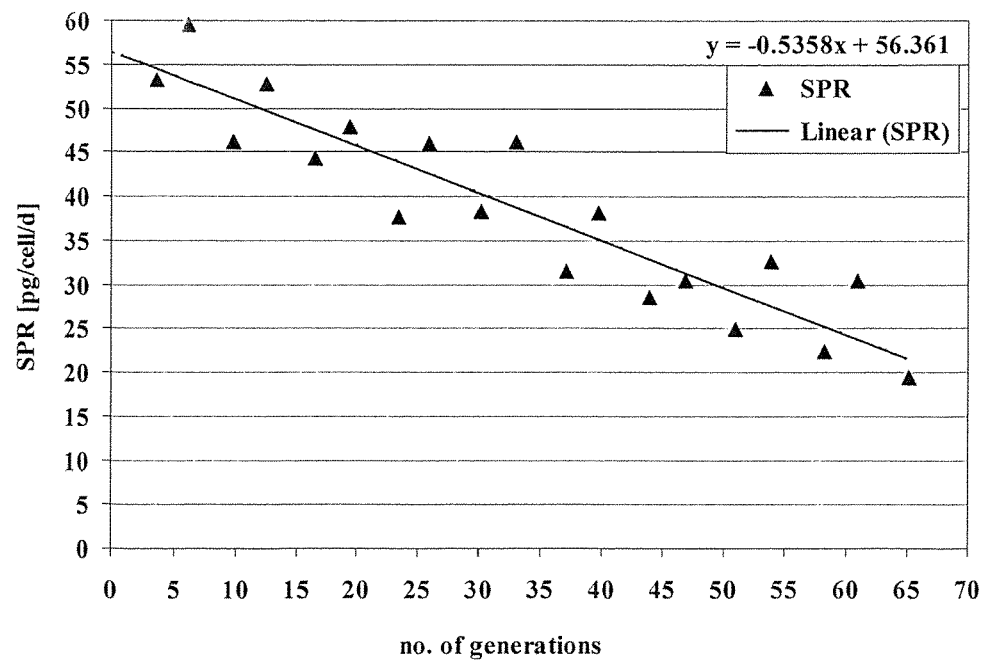
Figure 3C:
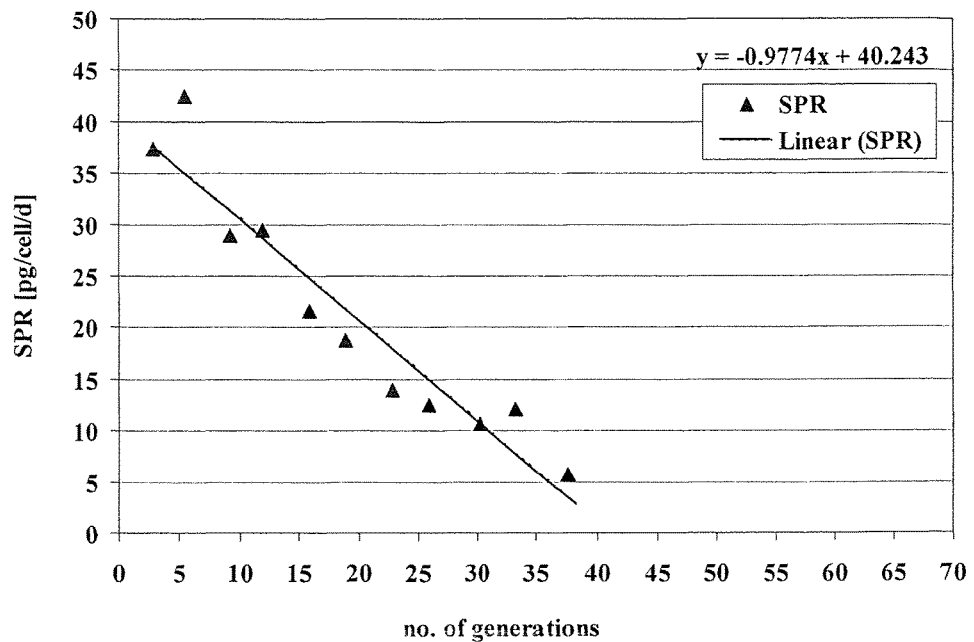
Figure 3D:
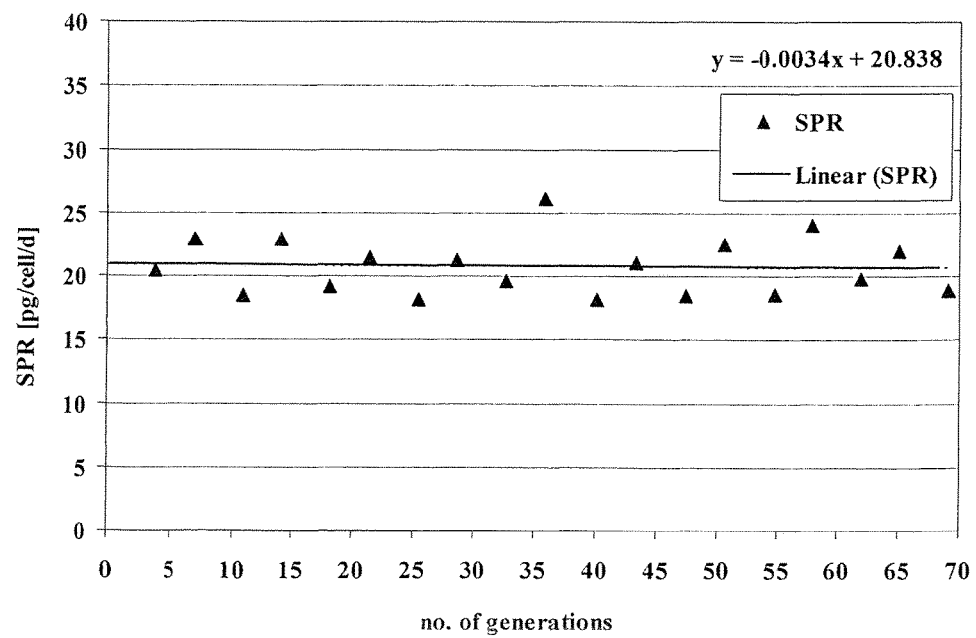
Figure 3E:
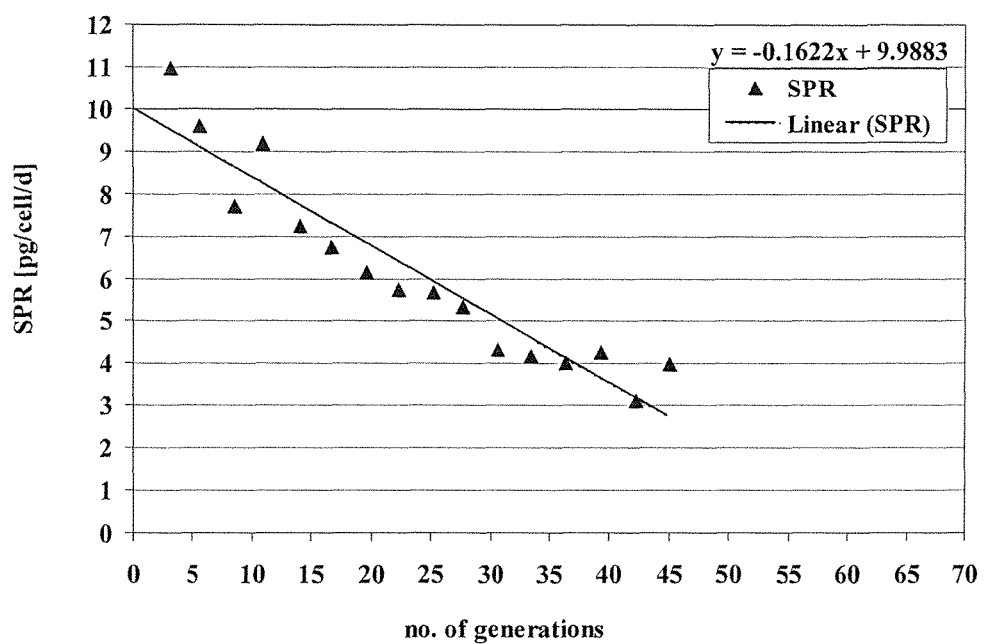

Recombinant cell lines expressing a human antibody of class IgG were generated by stable transfection of CHO-K1 or CHO-DG44 suspension growing cells with a vector encoding the light and heavy chain of antibody comprising a human immunoglobulin kappa light chain and a human immunoglobulin gamma 1 or gamma 4 heavy chain. The vector further comprised a nucleic acid encoding murine dihydrofolate reductase (DHFR) (FIG. 2). Light and heavy chain expression cassettes were both under the control of a human CMV immediate-early promoter and enhancer (SEQ ID NO: 1). Transfection of cells was either performed by nucleofection (Lonza Cologne GmbH or Amaxa Biosystems) or by electroporation using Gene Pulser XCell (BIO-RAD).

For example, CHO-K1 or CHO-DG44 suspension were transfected with linearized plasmid DNA, using the Nucleofector device in combination with the Nucleofector Kit V (Lonza Cologne GmbH, Cologne, Germany) or by electroporation using the Gene Pulser XCell (Bio-Rad, Hercules, Calif.), according to the manufacturers' protocols. Transfected cells were seeded into 96 or 384-well plates containing thymidine-free medium with various concentrations of methotrexate (MTX) as selection agent. After three weeks, antibody-expressing cell lines were identified by measuring antibody titers in the culture medium by ELISA. Top producers were expanded to higher volumes, subcloned by limiting dilution and cryoconserved.

Stably transfected cells were selected in thymidine and protein free medium containing 20 nM to 1200 nM Methotrexate (MTX) as selection agent. Antibody expressing cells or cell lines were identified by measuring antibody titers in the culture medium and subcloned by limiting dilution and/or FACS single cell deposition.

The cells were propagated in disposable 50 ml vented shake flasks under standard humidified conditions (95% rH, 37° C., and 5% to 8% $CO_2$) at a constant agitation rate of 120 rpm/min to 150 rpm/min. Every 3-4 days the cells were split into fresh medium. Density and viability of the cultures were determined using the CASY TT or Cedex HiRes cell counter (Roche Innovates AG, Bielefeld, Germany).

Furthermore, standard cell culture techniques were applied as described e.g. in Current Protocols in Cell Biology, Bonifacino, J. S. et al. (eds), John Wiley & Sons, Inc., New York (2000).

EXAMPLE 3

Long-Term Cultivation and Production

Five CHO cell lines obtained according to Example 2 were investigated for long-term productivity: cell line K18.1 is derived from a CHO-K1 cell and produces an antibody of human subclass IgG1; cell lines G25-10, G25-17 and G42-5 are each derived from a CHO-K1 cell and produce an antibody of human subclass IgG4; cell line 43-16 A10 is derived from a CHO-DG44 cell and produce an antibody of human subclass IgG4.

The cells were tested for phenotypic, i.e. production, stability for 35 to 70 generations in the absence of a selection agent. The cells were continuously cultivated in vented 125 ml shake flasks containing 50 ml medium without MTX and diluted twice a week with fresh medium. Seeding density was 2 to $3 \times 10^5$ cells/ml. Prior to passage viable cell density and viability were determined. The age of the culture in generations at the end of each passage was calculated according to the following equitation:

$$a_2 = a_1 + \ln(D_2/D_1)/\ln 2 \qquad \text{(Formula 1)}$$

with $a_2$ [no. of generations]: age of the culture at the end of the passage, $a_1$ [no. of generations]: age of the culture at the beginning of the passage i.e. age of the culture at the end of the previous passage, $D_1$ [cells/ml]: viable cell density at the beginning of the passage, D2 [cells/ml]: viable cell density at the end of the passage.

Antibody concentration in the supernatant (antibody titer) was determined by protein A HPLC at the end of each passage. From these data, the specific production rate (SPR) for each passage was calculated using the following formula:

$$SPR = P_2 - P_1/((D_2-D1)/2*\Delta t) \quad \text{(Formula 2)}$$

with

SPR [pg/cell/d]: specific production rate, $P_1$ [µg/ml]: antibody titer at the beginning of the passage, $P_2$ [g/ml]: antibody titer at the end of the passage, $D_1$ [cells/ml]: viable cell density at the beginning of the passage, $D_2$ [cells/ml]: viable cell density at the end of the passage, $\Delta t$ [d]: duration of the passage.

The SPR values were plotted against the age of culture at the end of the respective passage in generations. A linear trend line was calculated over all SPR data points and the relative alteration of the SPR (in percent) over the period tested was calculated according to the following equitation:

$$\Delta SPR = m*a/SPR_0*100 \quad \text{(Formula 3)}$$

with

ΔSPR [%]: percentual alteration of SPR, m [pg/cell/d/generation]: slope of linear trend line, a [no. of generations]: age of culture, $SPR_0$: y-axis intercept of linear trend line.

Cell line G42-5 showed no change of SPR over the complete period tested (nearly 70 generations). All other cell lines showed a decrease in productivity already after 30 generations. The decrease ranged from 29% to 73%. For cell lines G25-17, G42-5 and 43-16 A10 the cultivating was stopped after 35 to 45 generations (FIGS. 3A to 3E, Tables 1 and 2).

TABLE 1

Change in SPR during cultivation of five cell lines in the absence of MTX.

| | Cell line K18.1 | Cell line G25-10 | Cell line G25-17 | Cell line G42-5 | Cell line 43-16 A10 |
|---|---|---|---|---|---|
| ΔSPR (30 generations) | −59% | −29% | −73% | 0% | −49% |
| ΔSPR (60 generations) | n.d. | −57%. | n.d. | −1% | n.d. | n.d. = not determined.

TABLE 2

Remaining SPR during cultivation of five cell lines in the absence of MTX. 100% = SPR at first generation.

| | Cell line K18.1 | Cell line G25-10 | Cell line G25-17 | Cell line G42-5 | Cell line 43-16 A10 |
|---|---|---|---|---|---|
| SPR (30 generations) | 41% | 71% | 27% | 100% | 51% |
| SPR (60 generations) | n.d. | 43% | n.d. | 99% | n.d. | n.d. = not determined

EXAMPLE 4

Identification of Methylated CpG Sites within Human CMV Immediate-Early Promoter/Enhancer DNA by Bisulfite Treatment and DNA Sequencing The human CMV immediate-early promoter/enhancer fragment (SEQ ID NO: 01) used for the expression of antibody light and heavy chain genes contains 33 CpG sites.

Genomic DNA was isolated from the CHO cell lines K18.1, G25-10, G25-17, G42-5 and 43-16 A10 using the Allprep DNA/RNA Mini Kit from Qiagen (Hilden, Germany). Five microgram DNA was cleaved with the enzyme Dra I and quantified by measuring the extinction at 260 nm. One hundred nanogram DNA was subjected to bisulfite treatment and purified using the EpiTect Bisulfite Kit (Qiagen, Hilden, Germany). Bisulfite treated DNA was recovered in 20 µl RNAse-free water (Qiagen, Hilden, Germany).

In order to amplify strand A (forward) of the human CMV immediate-early promoter/enhancer fragment (SEQ ID NO: 02), 1 µl bisulfite treated DNA was combined with 24 τl PCR master mix and subjected to PCR using the GeneAmp® PCR System 9700 (Applied Biosystems Inc., USA). 24 µl PCR master mix comprised:

1 µl forward primer 227 of SEQ ID NO: 06 (10 pmol/µl),
1 µl reverse primer 229 of SEQ ID NO: 08 (10 pmol/µl),
22 µl Platinum® PCR SuperMix HighFidelty (Invitrogen Corp., USA).

Forward primer 227 is complementary to the 5′-end of the human CMV immediate-early promoter/enhancer fragment. Reverse primer 229 binds downstream within the 5′-UTR of the immunoglobulin genes.

The PCR conditions were as follows:

| | | temp. | duration |
|---|---|---|---|
| Step 1 | Denaturation | 95° C. | 10 min. |
| Step 2: PCR # cycles: 45 | Denaturation | 94° C. | 30 sec. |
| | Annealing | 50° C. | 2 min. |
| | Extension | 68° C. | 2 min. |
| Step 3 | Final Extension | 72° C. | 10 min. |
| Step 4 | Soak | 4° C. | indefinite |

The PCR product was checked for size and purity by agarose gel electrophoresis and cloned in the vector pCR4 (Invitrogen Corp., USA) using the TOPO TA cloning kit (Invitrogen Corp., USA). Plasmid clones were isolated and analyzed by restriction digest and agarose gel electrophoresis. For each cell line, 19 to 22 plasmids containing the insert were sequenced. In order to estimate the deamination efficiency of the bisulfite treatment at non CpG sites, the number of residual cytosine at non-CpG sites was determined. The percentual deamination efficiency was calculates as follows:

$$E_{mod} = 100 - (C_{res}/C_{total}*100) \quad \text{(Formula 4)}$$

with
$E_{mod}$ [%]: deamination efficiency,
$C_{res}$: number of residual cytosine at non-CpG sites in all inserts analyzed, PCR primers sites excluded,
$C_{total}$: number of cytosine in the non-bisulfite treated CMV promoter/enhancer fragment, PCR primer sites excluded, multiplied by the number of inserts analyzed, i.e. 107*20.

It was found that the deamination efficiency at non-CpG cytosine was greater than 99% in all samples (Table 3).

TABLE 3

Deamination efficiency at non-CpG cytosine.

| | Cell line K18.1 | Cell line G25-10 | Cell line G25-17 | Cell line G42-5 | Cell line 43-16 A10 |
|---|---|---|---|---|---|
| $E_{mod}$ | 99.1% | 99.3% | 99.5% | 99.3% | 99.3% |

Protection of 5-methyl cytosine from deamination was confirmed by bisulfite treatment and subsequent cloning and sequencing of plasmid DNA isolated from dcm⁺ E. coli. Dcm⁺ E. coli methylate the internal cytosine residues within the sequences CCAGG or CCTGG (dcm-sites). It was found that the deamination efficiency was 99% at non-dcm-sites and less than 5% at internal cytosine within dcm-sites.

To quantify the extend of DNA methylation at CpG sites within the bisulfite treated CMV promoter/enhancer fragment, the number of cytosine found at each CpG-site was determined and plotted for each analyzed cell.

Figure 4A:
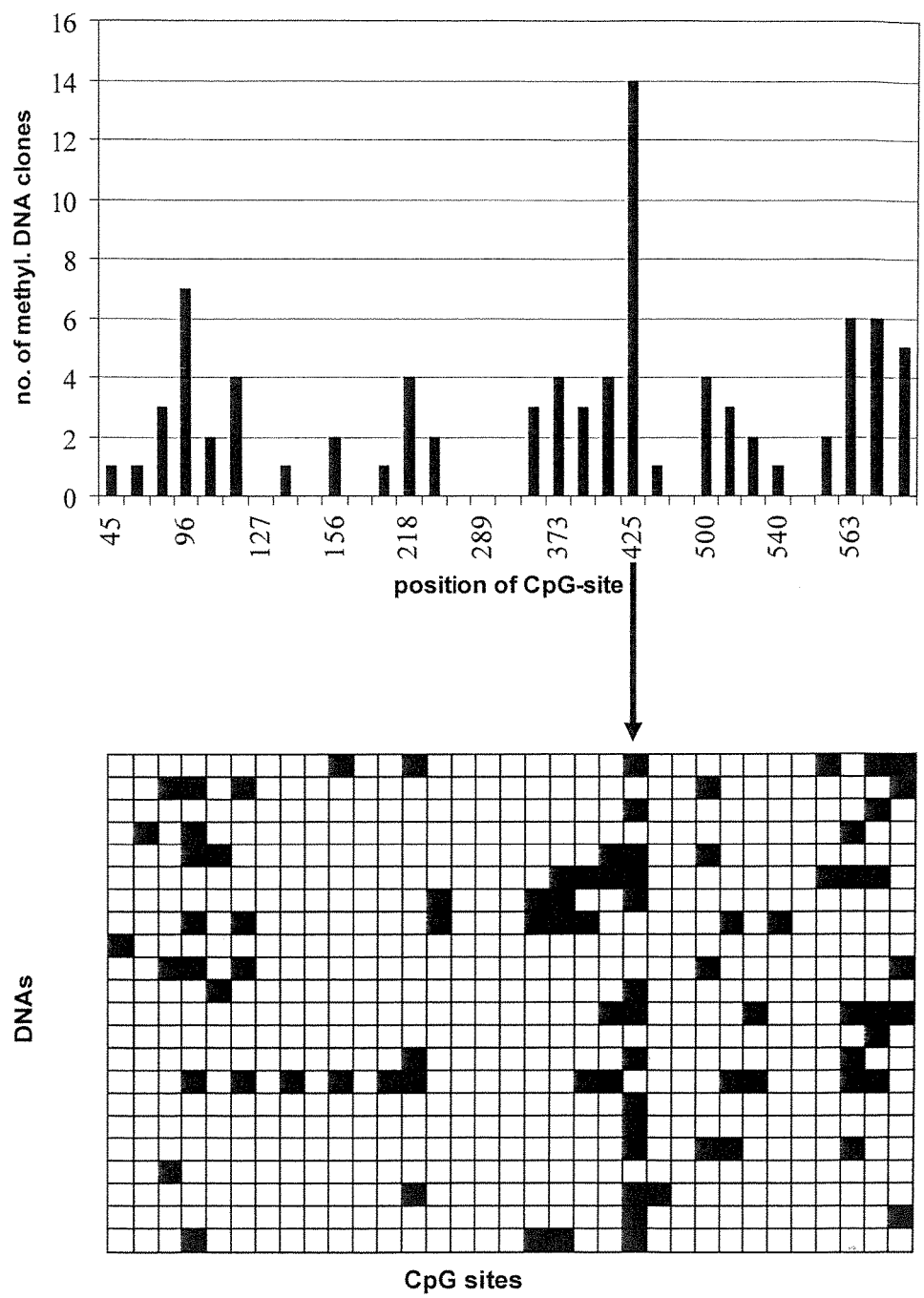
FIGS. 4A-E Upper figure: frequency of methylation within hCMV-MIE DNA from recombinant CHO cell lines at different methylation sites determined by the analysis of 19-22 individual promoter nucleic acids; lower figure: schematic representation of methylated CpG sites within hCMV-MIE promoter/enhancer DNA from recombinant CHO cell lines—methylated sites are shown in black—position 425 is highlighted by an arrow.

Cell line K18.1 is highly methylated (FIG. 4A). The frequency of methylation accumulates in 3 clusters, one at the 5'-end, one the 3'-end and one at around position 400. The highest degree of methylation was found at position 425. Fourteen out of the twenty-two inserts sequenced had a cytosine here.

Figure 4B:
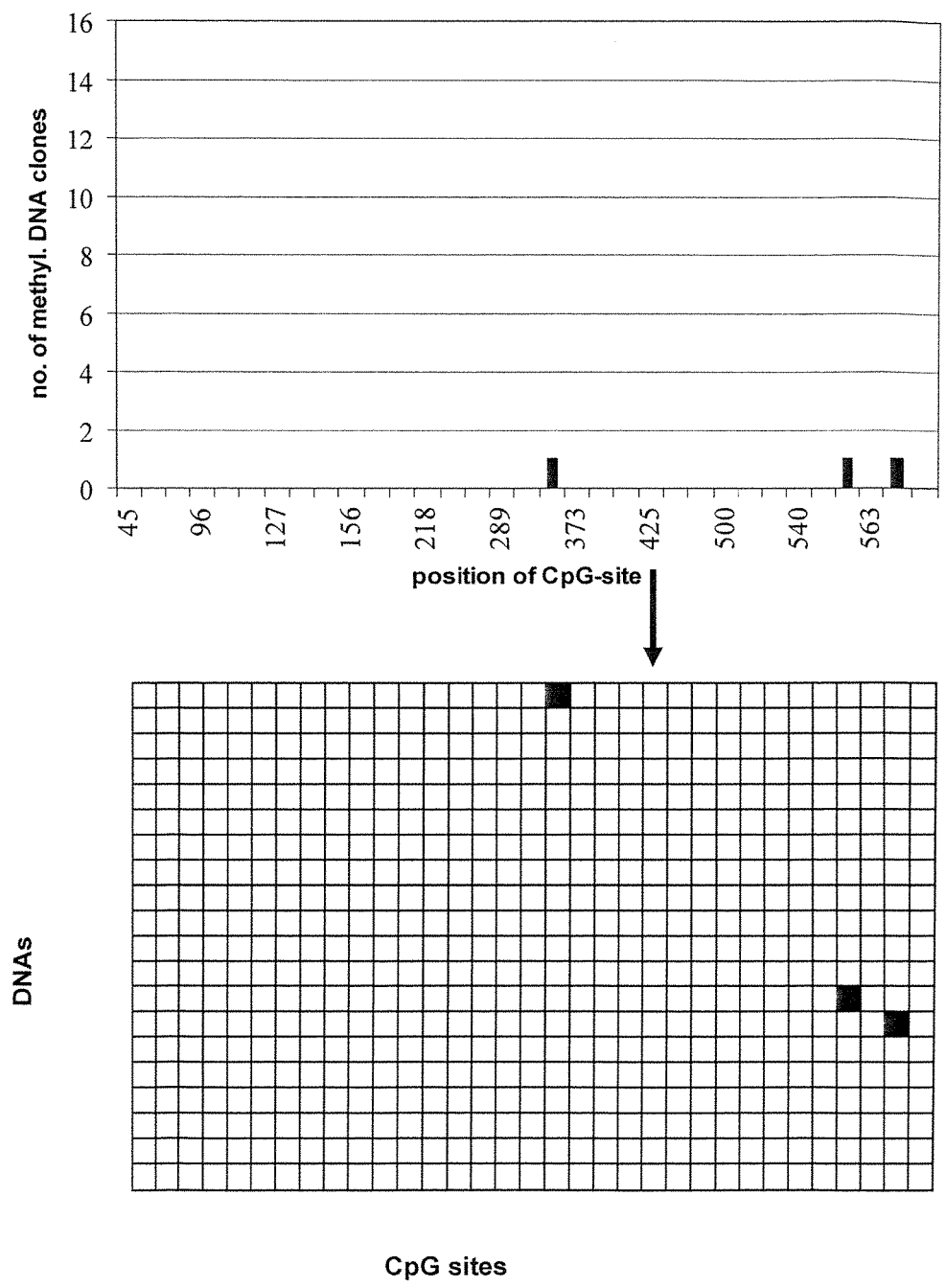
Figure 4C:
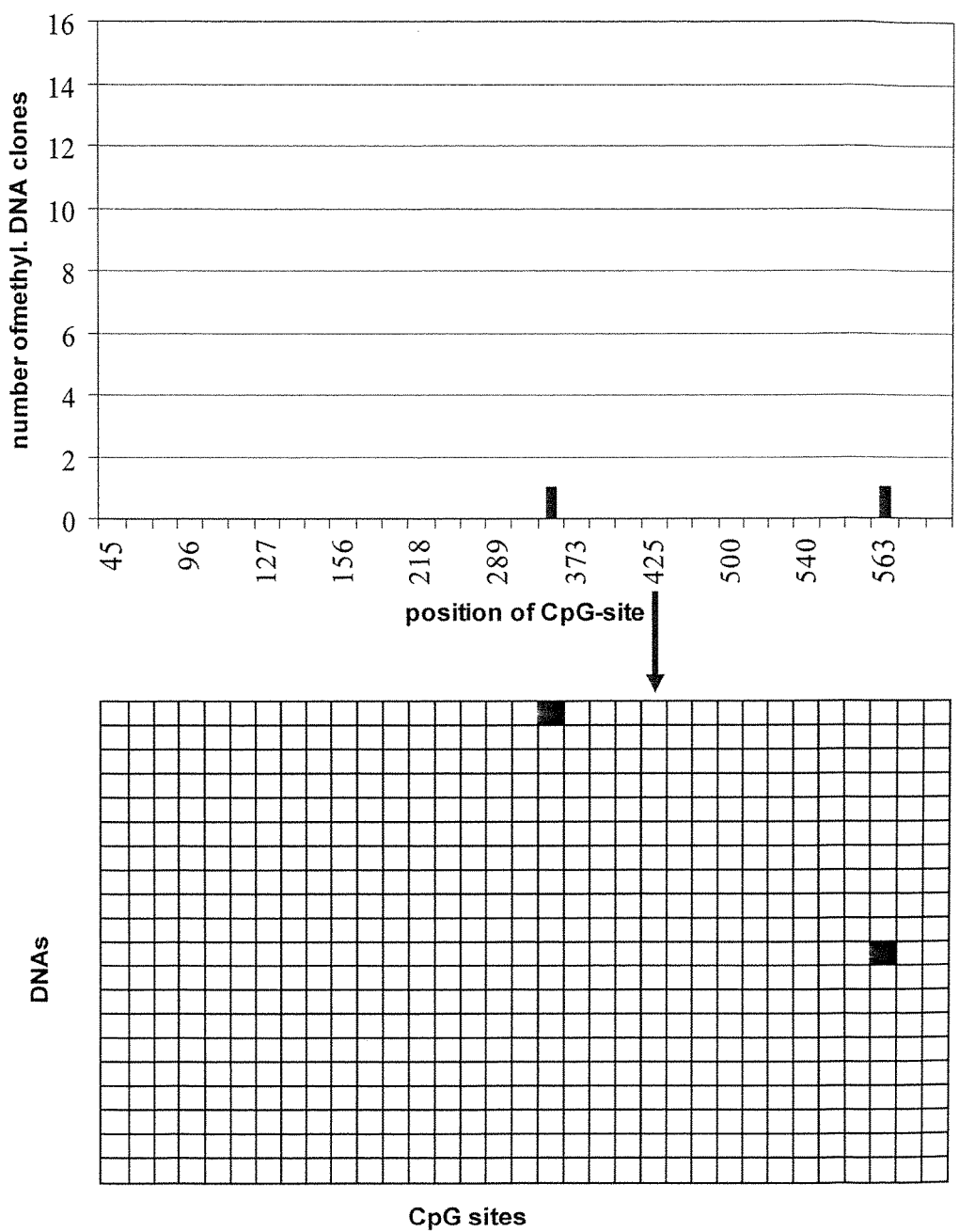
Figure 4D:
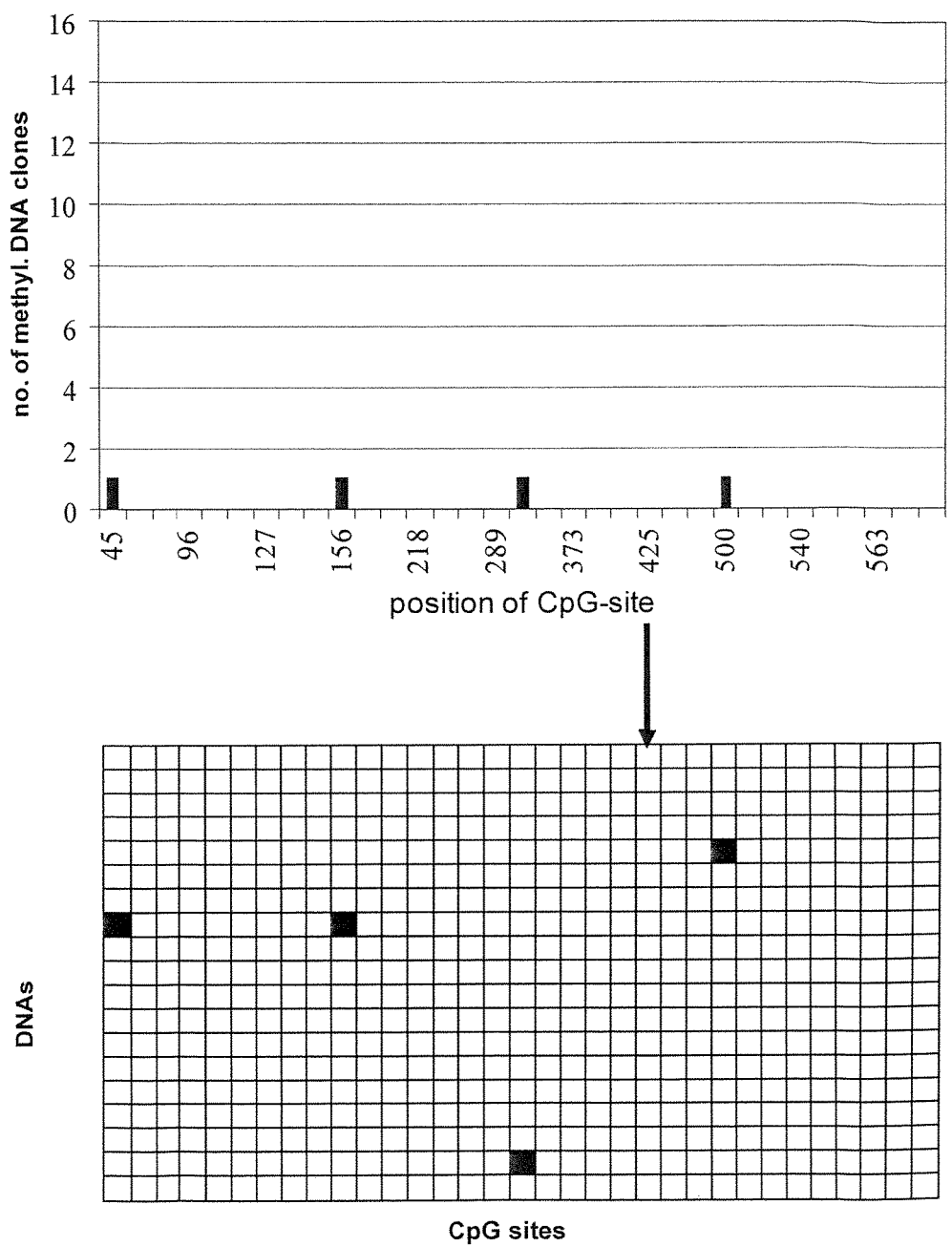
Figure 4E:
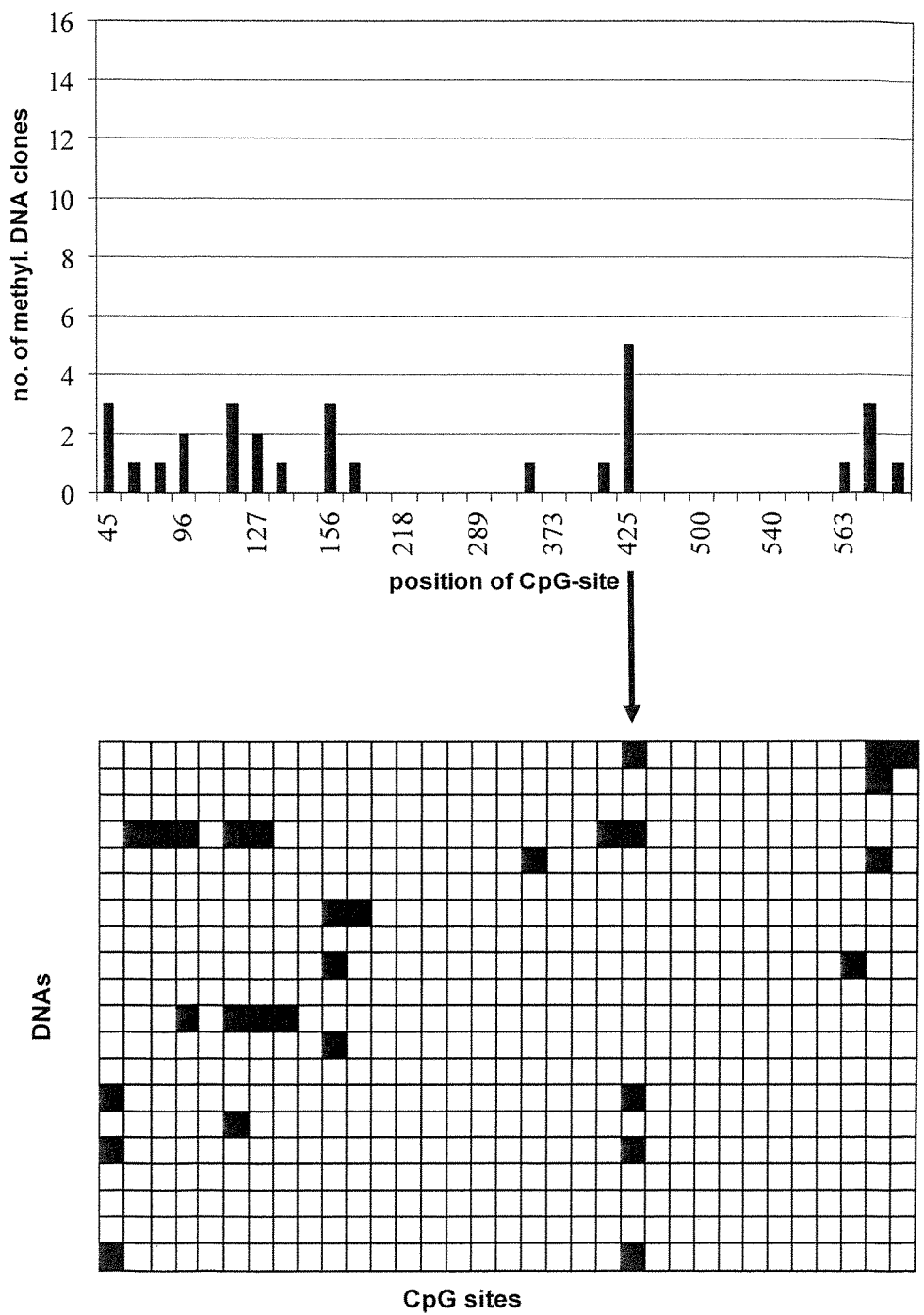
Figure 5A:
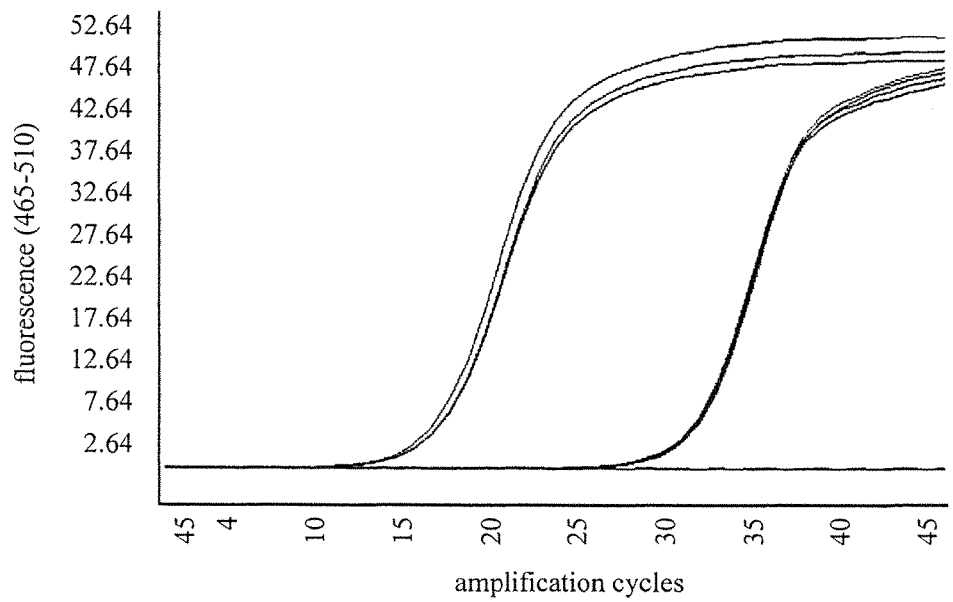
FIGS. 5A-D Discrimination of hCMV-MIE which is methylated at site 425 from hCMV-MIE which is non-methylated at site 425 by methylation specific real-time pPCR; PCR amplification curves for templates #11 (FIG. 5A), #62 (FIG. 5B), #01 (FIG. 5C) and #04 (FIG. 5D).
Figure 5B:
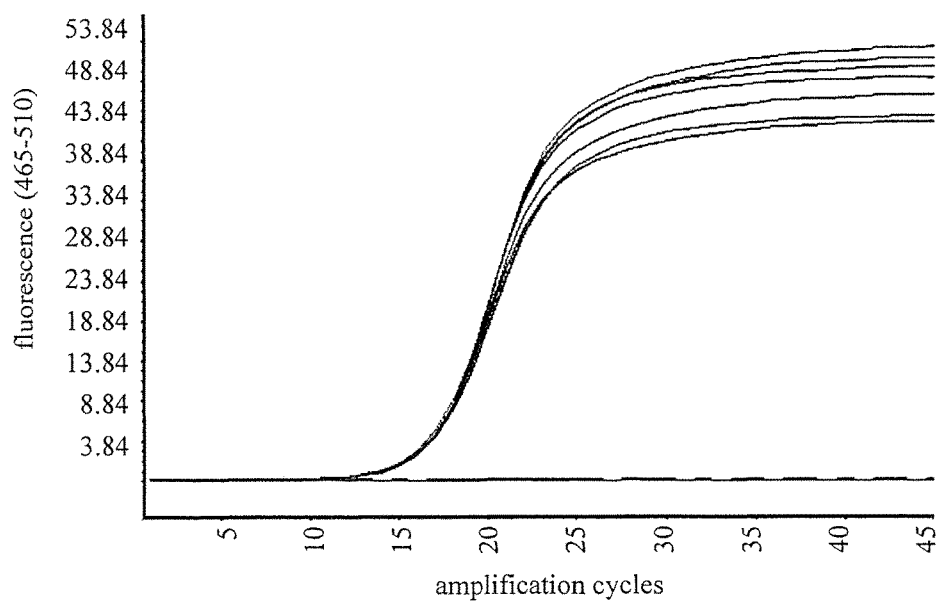
Figure 5C:
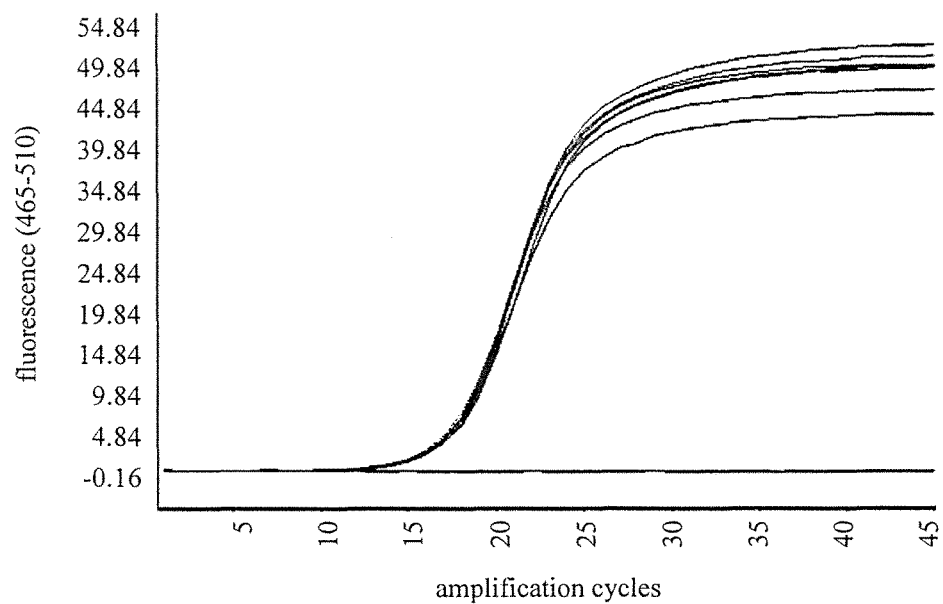
Figure 5D:
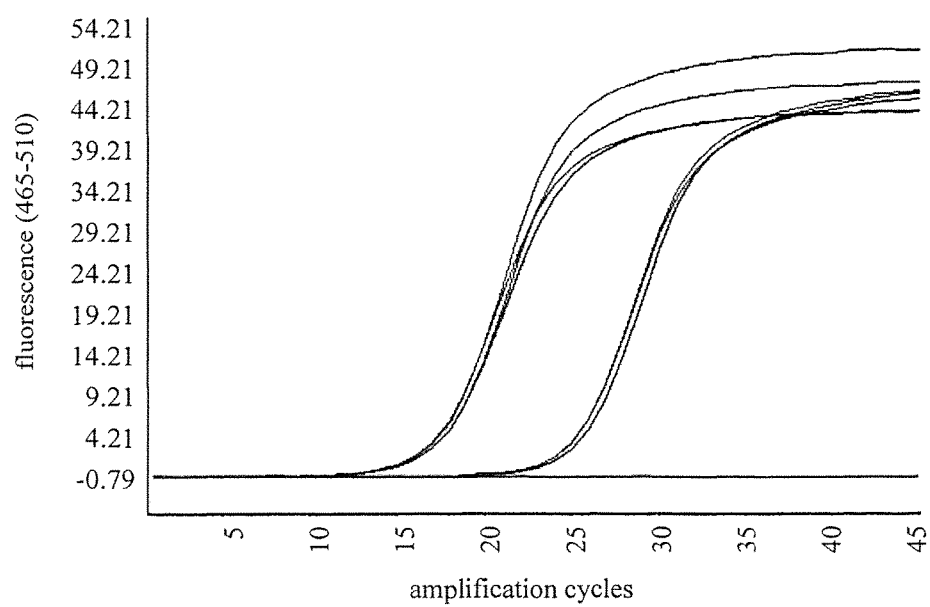

Methylation of the CMV promoter from cell line 43-16 A10 was noticeable (FIG. 4E). The distribution of methylation was similar to the distribution observed with cell line K18.1. Position 425 was methylated most often. Five of the twenty inserts sequenced contained a cytosine in this position.

In the three other cell lines investigated cytosine were detected only sporadically at CpG sites (FIGS. 4B, 4C and 4D).

EXAMPLE 5

Quantitative Methylation Specific PCR of Bisulfite Treated Human CMV Immediate-Early Promoter/Enhancer DNA In this example a methylation specific real-time qPCR as method to detect methylation at a CpG position, to be more precise at position 425 of the hCMV promoter nucleic acid, is reported.

Two sets of primers were designed:
a methylation specific primer pair (MSP primer pair) selectively amplifying deaminated CMV promoter DNA with a cytosine in position 425 representing DNA that is methylated at position 425, and
a universal primer pair amplifying deaminated CMV promoter DNA irrespective of the methylation status.

The universal primer pair was used for normalization. To be used in the same PCR run both primer pairs should have similar melting points.

The designing of primers sensing methylation at position 425 was complicated by the presence of two additional CpG sites in close proximity (position 416 and position 437). Methylation sensitive primers should detect 5mC425 independent of the methylation status of position 416 and position 437.

Four deaminated human CMV immediate-early promoter/enhancer fragments isolated in Example 4 representing the possible sequence variations in positions 425 and 437: #11, #62, #01 and #04 (Table 4, SEQ ID NO: 19, SEQ ID NO: 20, SEQ ID NO: 21, SEQ ID NO: 22) have been used as qPCR templates for methylation specific PCR and universal primer pairs.

TABLE 4

Expected results for MSP and universal primer pairs in qPCR.

| | Templates | | | |
|---|---|---|---|---|
| | #11 | #62 | #01 | #04 |
| Pos. 425 | T | C | C | T |
| Pos. 437 | T | C | T | C |
| | Amplification | | | |
| MSP primer pair | − | + | + | − |
| Universal primer pair | + | + | + | + |

With the universal primer all four templates can be comparably amplified whereas the methylation specific primer pair can selectively amplify template #62 and template #01. ΔCp should be as small as possible between the methylation specific primer pair and the universal primer pair on templates #62 and template #01. Cp values obtained with the methylation specific primer pair on template #11 and template #04 should be as high as possible, i.e. ΔCp compared to amplification with the universal primer pair should be maximal.

For qPCR the LightCycler® 480 II system was employed (Roche Diagnostics GmbH, Mannheim, Germany) and samples were prepared using the LightCycler® 480 SYBR Green I Master (Roche Diagnostics GmbH, Mannheim, Germany). Five microliters template solution containing 0.05 ng DNA was combined with 15 l PCR master mix in a well of a 96-well multi well plate.

15 µl PCR master mix comprised:
  4.2 µl water,
  0.4 µl forward primer 239, 263 or 264 (also possible primer 227, 228, 240, 238) (10 pmol/µl),
  0.4 µl reverse primer 237, 254, 262, 265, 266, 267 or 268 (also possible primer 229) (10 pmol/µl),
  10 µl SYBR Green I Master.

The multi well plate was sealed with a LightCycler® 480 sealing foil (Roche Diagnostics GmbH, Mannheim, Germany) and centrifuged at 1,500×g for 2 minutes. Afterwards the plate was mounted into the LightCycler® 480 system and subjected to qPCR. Each sample was tested in duplicate, triplicate or quadruplicate. To allow determination of absolute copy numbers, standard curves were generated for the LC and the HC transgene, using the linearized expression plasmid as standard. Standard dilutions contained $2.5 \times 10^7$, $2.5 \times 10^6$, $2.5 \times 10^5$, $2.5 \times 10^4$ or $2.5 \times 10^3$ plasmid copies. Genomic DNA was tested in triplicate; standards were run in quadruplicate.

PCR conditions were as follows:

| step | | No. of cycles | T [° C.] | t [min:s] | ramp rate [° C. s − 1] | acquisition |
|---|---|---|---|---|---|---|
| denaturation | | 1 | 95 | 10:00 | 4.40 | — |
| real-Time PCR | denaturation | 45 | 95 | 00:10 | 4.40 | — |
| | annealing | | 57 to 59 | 00:15 | 2.20 | — |
| | elongation | | 72 | 00:07 | 4.40 | — |
| | detection | | 66 | 00:01 | 2.20 | single |
| melting curve | denaturation | 1 | 95 | 00:05 | 4.40 | — |
| | annealing | | 60 | 01:00 | 2.20 | — |
| | melting | | 90 | 00:00 | 0.11 | continuous |
| cooling | | 1 | 40 | 00:30 | 2.2 | |

The collection and analysis of the data was done with the LightCycler® 480 software version 1.5. The apparent degree of methylation was calculated using the following formula, where ideal amplification efficiency was assumed (E=2).

$$mC_{app} = 2^{Cp(t)-Cp(m)} * 100 \quad \text{(Formula 5)}$$

with $mC_{app}$ [%]: apparent degree of methylation,
$Cp(t)$: Cp value obtained with universal primers,
$Cp(m)$: Cp value obtained with methylation-specific primers.

Figure 6:
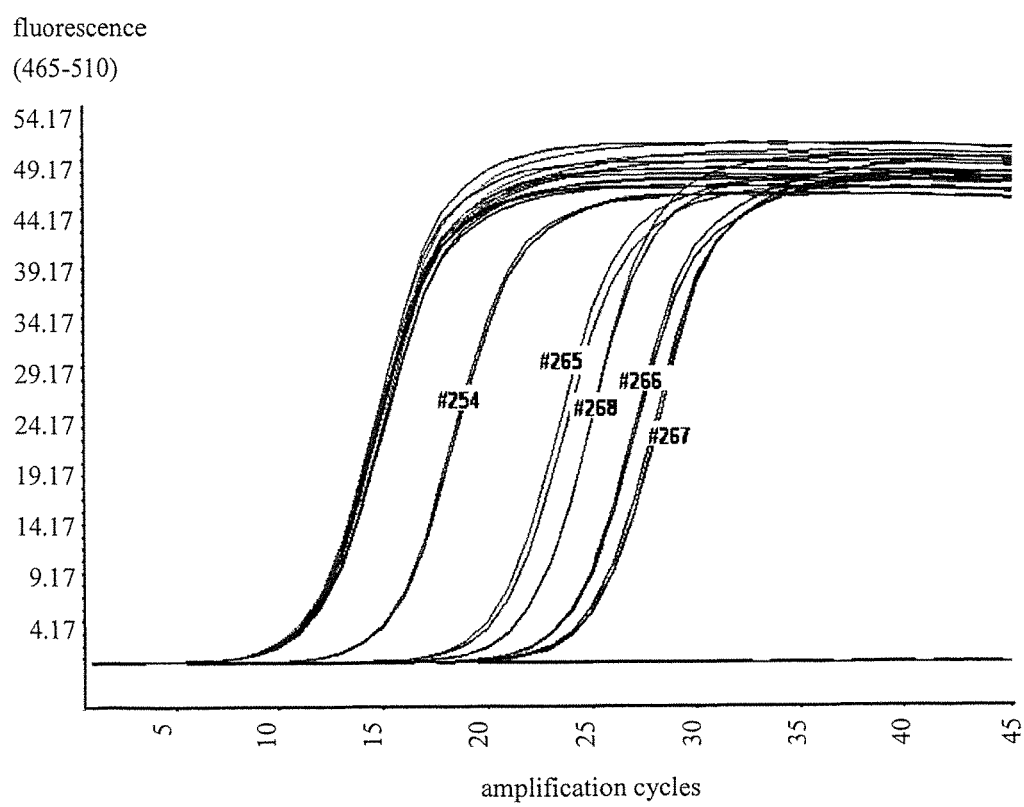
FIG. 6 PCR amplification curves for different methylation specific primer and primer pairs.

During primer evaluation, it was found that designing methylation specific primer, which are highly selective for deaminated CMV promoter DNA with a cytosine at position 425 ("methylated"), has to be performed with care. Primer 266 and 267 showed the maximal difference between Cp(#11) and Cp(#62), i.e. the highest selectivity for "methylated" DNA. Primer 265, 268 and 254 showed minor selectivity. The universal primer pair 263/237 was tested as control for minimal ΔCp (FIG. 6 and Table 5).

TABLE 5

Results of primer evaluation.

| Primer | Template | Mean Cp | STD Cp | ΔCp [Cp(#11) − Cp(#62)] | Stdv. ΔCp [Cp(#11) − Cp(#62)] |
|---|---|---|---|---|---|
| 263 + 237 | #11 | 11.71 | 0.06 | 0.23 | 0.06 |
| | #62 | 11.48 | 0.01 | | |
| 263 + 254 | #11 | 15.22 | 0.08 | 3.89 | 0.19 |
| | #62 | 11.32 | 0.17 | | |
| 263 + 265 | #11 | 20.29 | 0.23 | 8.74 | 0.23 |
| | #62 | 11.55 | 0.02 | | |
| 263 + 266 | #11 | 23.76 | 0.04 | 12.31 | 0.16 |
| | #62 | 11.45 | 0.16 | | |
| 263 + 267 | #11 | 24.74 | 0.14 | 13.05 | 0.16 |
| | #62 | 11.69 | 0.07 | | |
| 263 + 268 | #11 | 21.75 | 0.06 | 10.25 | 0.10 |
| | #62 | 11.51 | 0.09 | | |

In FIGS. 5A-D the results obtained with the methylation specific primer pair 239/267 (SEQ ID NO: 11, SEQ ID NO: 18) in combination with the universal primer pair 239/237 (SEQ ID NO: 11, SEQ ID NO: 09) is shown. Universal primer pair 239/237 amplified all four templates about equally well, whereas the methylation specific primer pair 239/267 amplified templates #62 and #01. Templates #11 and #4 are only poorly amplified by the primer pair 239/267.

Methylation frequency calculated from the Cp values was almost 100% for template #62 and template #01 and almost 0% for template #11 and template #04 (Table 6A). This shows that methylation specific primer pair 239/267 in combination with the universal primer pair 239/237 can be used to discriminate CMV promoter DNA which is methylated at position 425 from CMV promoter DNA which is non-methylated at position 425 by real-time qPCR.

Additional universal and methylation specific primer pairs were found and are characterized in Table 6A and 6B.

TABLE 6A

Methylation specific reverse primer 267 and non-methylation specific reverse primer 237 combined with three different forward primer.

| | | | universal primer pairs | | | | | |
|---|---|---|---|---|---|---|---|---|
| | methylation site | | 239 (for) + 237 (rev) | | 263 (for) + 237 (rev) | | 264 (for) +237 (rev) | |
| template | 425 | 437 | Cp(u) | Stdv | Cp(u) | Stdv | Cp(u) | Stdv |
| # 11 | T | T | 16.41 | 0.23 | 15.65 | 0.01 | 15.73 | 0.1 |
| # 62 | C | C | 16.73 | 0.04 | 16 | 0.08 | 16.38 | 0.25 |
| # 01 | C | T | 17.51 | 0.24 | 16.64 | 0.08 | 16.87 | 0.21 |
| # 04 | T | C | 17.58 | 0.24 | 16.18 | 0.16 | 16.54 | 0.22 |

| | | | C425 specific primer pairs | | | | | |
|---|---|---|---|---|---|---|---|---|
| | methylation site | | 239 (for) + 267 (rev) | | 263 (for) + 267 (rev) | | 264 (for) + 267 (rev) | |
| template | 425 | 437 | Cp(m) | Stdv | Cp(m) | Stdv | Cp(m) | Stdv |
| # 11 | T | T | 30.71 | 0.23 | 26.84 | 0.28 | 28.01 | 0.14 |
| # 62 | C | C | 16.74 | 0.13 | 16 | 0.38 | 16.82 | 0.29 |
| # 01 | C | T | 17.52 | 0.18 | 16.91 | 0.36 | 17.06 | 0.17 |
| # 04 | T | C | 25.34 | 0.24 | 23 | 0.14 | 23.68 | 0.27 |

| | methylation site | | ΔCp = Cp(m) − Cp(u) | | | | | |
|---|---|---|---|---|---|---|---|---|
| template | 425 | 437 | ΔCp | Stdv | ΔCp | Stdv | ΔCp | Stdv |
| # 11 | T | T | 14.3 | 0.33 | 11.19 | 0.28 | 12.28 | 0.17 |
| # 62 | C | C | 0.01 | 0.14 | 0 | 0.39 | 0.44 | 0.38 |
| # 01 | C | T | 0.01 | 0.30 | 0.27 | 0.37 | 0.19 | 0.27 |
| # 04 | T | C | 7.76 | 0.34 | 6.82 | 0.21 | 7.14 | 0.35 |

TABLE 6A-continued

Methylation specific reverse primer 267 and non-methylation specific reverse primer 237 combined with three different forward primer.

| | methylation site | | mCapp [%] | | | | | |
|---|---|---|---|---|---|---|---|---|
| template | 425 | 437 | mCapp | Stdv | mCapp | Stdv | % rel. | Stdv |
| # 11 | T | T | 0.0 | 0.0 | 0.0 | 0.0 | 0.0 | 0.0 |
| # 62 | C | C | 99.3 | 9.4 | 100.0 | 26.9 | 73.7 | 19.6 |
| # 01 | C | T | 99.3 | 20.7 | 82.9 | 21.2 | 87.7 | 16.4 |
| # 04 | T | C | 0.5 | 0.1 | 0.9 | 0.1 | 0.7 | 0.2 |

TABLE 6B

Methylation specific reverse primer 266 and non-methylation specific reverse primer 237 combined with two different forward primer.

| | methylation site | | universal primer pairs | | | |
|---|---|---|---|---|---|---|
| | | | 263 (for) + 237 (rev) | | 264 (for) + 237 (rev) | |
| template | 425 | 437 | Cp(u) | Stdv | Cp(u) | Stdv |
| # 11 | T | T | 15.32 | 0.18 | 15.88 | 0.08 |
| # 62 | C | C | 15.73 | 1.07 | 16.22 | 0.57 |
| # 01 | C | T | 15.42 | 0.19 | 16.35 | 0.22 |
| # 04 | T | C | 15.4 | 0.24 | 16.8 | 1.12 |

| | methylation site | | C425 specific primer pairs | | | |
|---|---|---|---|---|---|---|
| | | | 263 (for) + 267 (rev) | | 264 (for) + 267 (rev) | |
| template | 425 | 437 | Cp(m) | Stdv | Cp(m) | Stdv |
| # 11 | T | T | 28.33 | 0.62 | 28.27 | 0.44 |
| # 62 | C | C | 15.64 | 0.25 | 16.32 | 0.35 |
| # 01 | C | T | 15.83 | 0.34 | 16.59 | 0.01 |
| # 04 | T | C | 22.39 | 0.15 | 22.83 | 0.88 |

| | methylation site | | ΔCp = Cp(m) − Cp(t) | | | |
|---|---|---|---|---|---|---|
| template | 425 | 437 | ΔCp | Stdv | ΔCp | Stdv |
| # 11 | T | T | 13.01 | 0.65 | 12.39 | 0.45 |
| # 62 | C | C | −0.09 | 1.10 | 0.1 | 0.67 |
| # 01 | C | T | 0.41 | 0.39 | 0.24 | 0.22 |
| # 04 | T | C | 6.99 | 0.28 | 6.03 | 1.42 |

| | methylation site | | mCapp [%] | | | |
|---|---|---|---|---|---|---|
| template | 425 | 437 | mCapp | Stdv | % rel. | Stdv |
| # 11 | T | T | 0.0 | 0.0 | 0.0 | 0.0 |
| # 62 | C | C | 106.4 | 81.1 | 93.3 | 43.3 |
| # 01 | C | T | 75.3 | 20.3 | 84.7 | 12.9 |
| # 04 | T | C | 0.8 | 0.2 | 1.5 | 1.5 |

For quantification of the degree of methylation over a broad range template #62 was mixed in different ratios with template #11. qPCR was performed as described above using primer pairs 239/237 and 239/267 and the recovery of template #62 in the template #11 background was calculated.

For calculation of the fraction of template #62 DNA, the amplification efficiencies of the primer pairs under the used conditions were determined. Serial dilutions of templates #62 and #11 from n=0.005 ng to 0.5 ng DNA were subjected to qPCR and the determined Cp values were plotted against log (n). A linear regression line was calculated using XLfit (Microsoft). The amplification efficiency was calculated using the following formula:

$$E = 10^{-1/m} \quad \text{(Formula 6)}$$

with
E: amplification efficiency,
m: slope of linear trend line.

The amplification efficiencies of both primer pairs were calculated to be approximately 1.7. The following formula was employed for calculating the fraction of template #62 DNA:

$$mC = 1.7^{Cp(t)-Cp(m)} * 100 \quad \text{(Formula 7)}$$

with
mC [%]: fraction of DNA methylated at position 425,
Cp(t): Cp value obtained with universal primer pair,
Cp(m): Cp value obtained with methylation specific primer pair.

Figure 7:
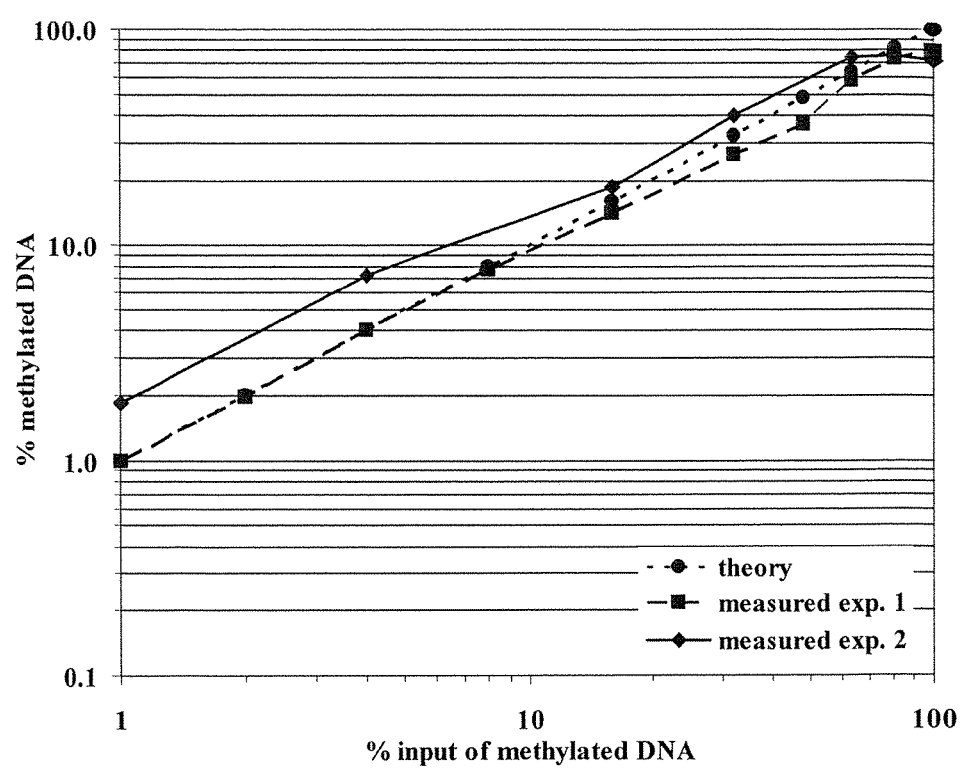
FIG. 7 Recovery of site 425 methylated hCMV-MIE in the background of non-methylated hCMV-MIE by methylation specific real-time qPCR.

The determined fractions of template #62 DNA from two independent experiments were plotted against the expected values (FIG. 7). Quantification of methylation between 1% and 100% can be performed.

EXAMPLE 6

Human CMV Immediate-Early Promoter/Enhancer Methylation Correlation with Long-Term Productivity a) Methylation Specific qPCR with Pre-Amplified Human CMV Immediate-Early Promoter/Enhancer Strand A As reported in Example 4 genomic DNA was isolated from CHO cell lines K18.1, G25-10, G25-17, G42-5 and 43-16 A10, cleaved with the enzyme DraI and deaminated by bisulfite treatment. The strand A of the human CMV immediate-early promoter/enhancer was amplified using primer 227 and 229.

The PCR product was diluted 1:50,000. Five microliters of each dilution were used for real-time qPCR. Primer 239 and 237 were employed for quantification of total CMV promoter DNA; primer 239 and 267 were employed for quantification of CMV promoter/enhancer DNA methylated at position 425. Samples were tested in triplicates. Templates #11, #62 and #01 were used as controls.

The qPCR was set up as reported in Example 5 by combining 5 μl template with 15 μl PCR master mix. The PCR conditions were as reported in Example 5. The primer annealing temperature was 58° C.

b) Methylation Specific qPCR with Bisulfite Treated Genomic DNA

Genomic DNA was extracted from CHO cell lines K18.1, G25-10, G25-17, G42-5 and 43-16 A10, cleaved with the enzyme DraI and deaminated by bisulfite treatment. Two microliters deaminated DNA diluted in 3 μl water was used as template in real-time qPCR applying primer pair 239/237 for amplification of total CMV promoter/enhancer strand A and primer pair 239/267 for amplification of CMV promoter/ enhancer strand A methylated at position 425. Samples were tested in triplicates. Templates #11 and #62 were used as controls.

The PCR was set up and qPCR was performed as reported in Example 5. The primer annealing temperature was 58° C.

For a) and b) the fraction of promoter DNA methylated at position 425 was calculated as follows:

$$mC = 1.7^{Cp(t)-Cp(m)} * 100 \quad \text{(Formula 7)}$$

with
- mC [%]: fraction of DNA methylated at position 425,
- Cp(t): Cp value obtained with universal primer pair 239/237,
- Cp(m): Cp value obtained with methylation-specific primer pair 239/267.

Figure 8A:
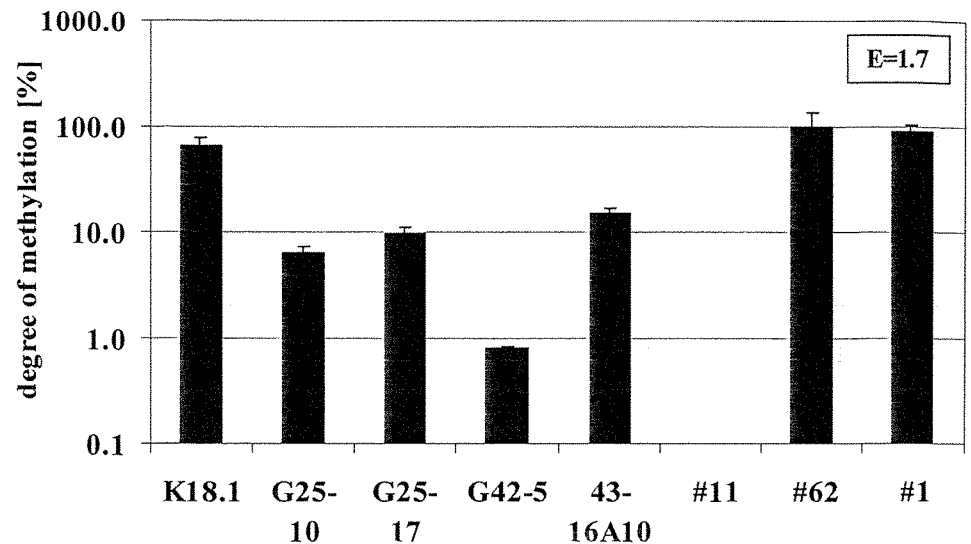
FIGS. 8A-B CMV promotor nucleic acid methylation at methylation site 425 obtained with primer #239 and #267 with pre-amplification (FIG. 8A) and directly from bisulfite treated genomic DNA (FIG. 8B).
Figure 8B:
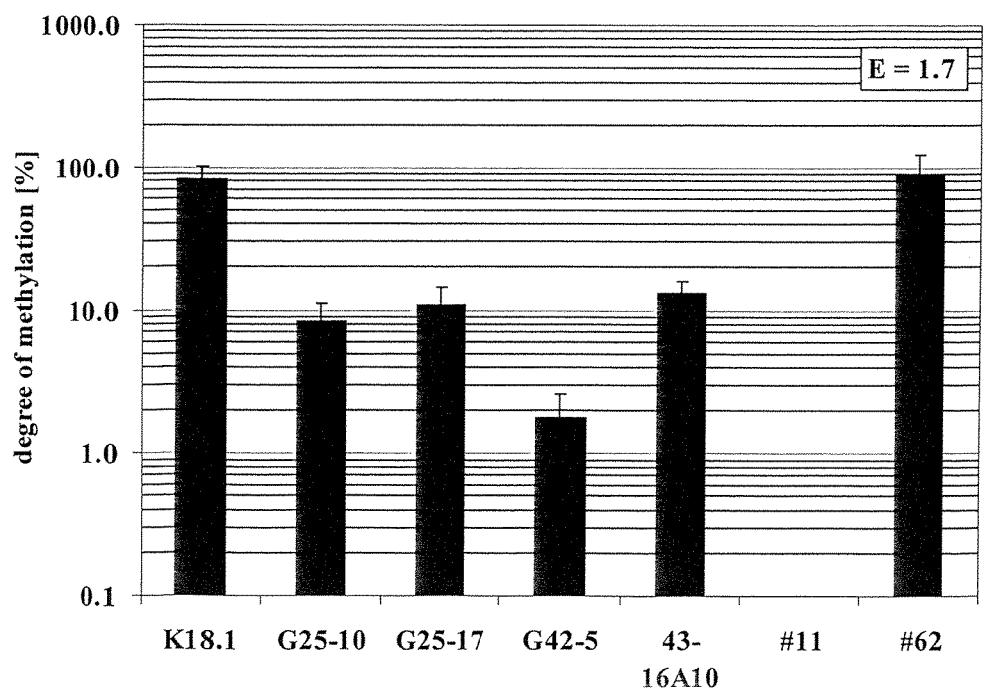
Figure 9:
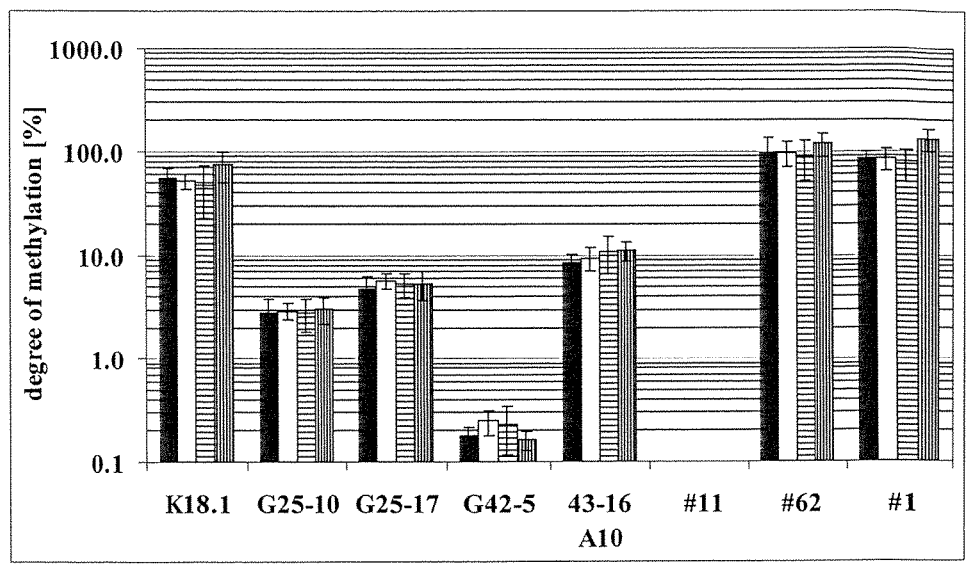
FIG. 9 CMV promotor nucleic acid methylation at methylation site 425 obtained with primer (black) 239+237 and 239+267, (white) 263+237 and 263+267, (horizontal lines) 264+237 and 264+267 and (vertical lines) 239+237 and 239+266.
Figure 10A:
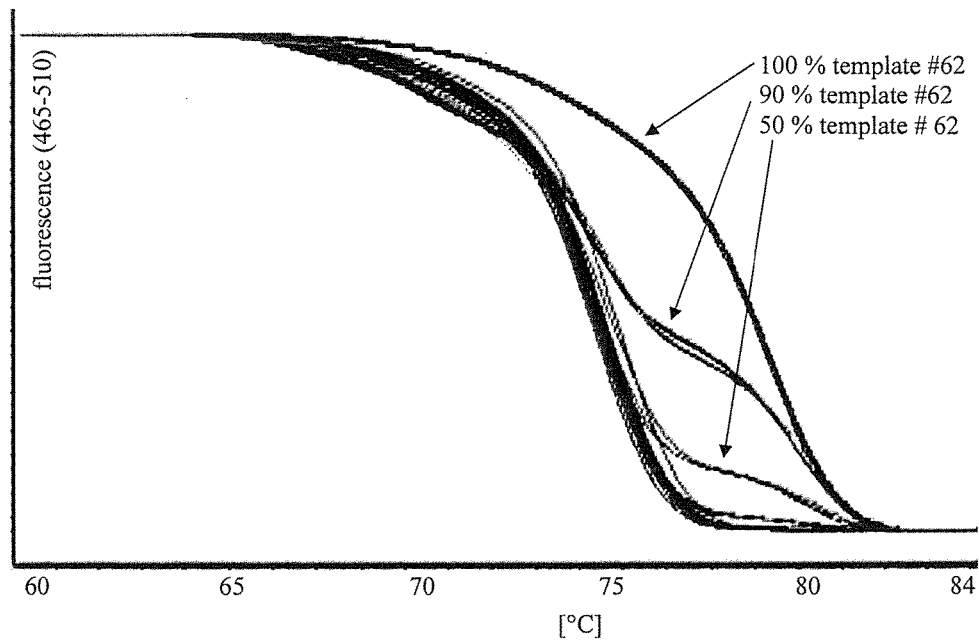
FIGS. 10A-B Exemplary high resolution normalized melting curve analysis (FIG. 10A) and first derivative thereof, i.e. melting peaks (FIG. 10B).
Figure 10B:
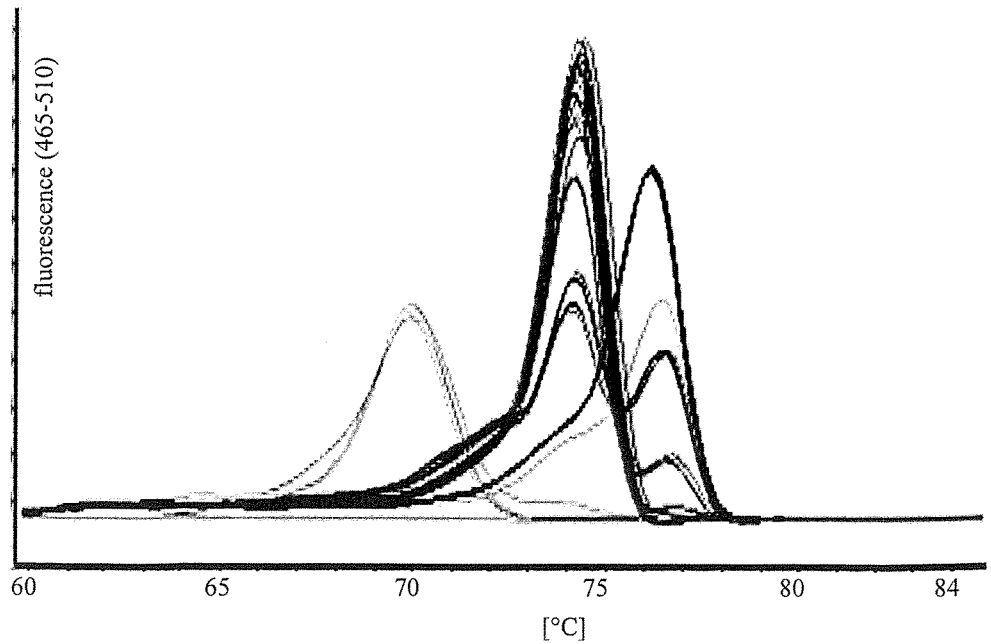

Both assay set-ups provided comparable results. The standard deviation within triplicates was higher without pre-amplification of the CMV promoter strand A (FIGS. 8A and 8B). Methylation of position 425 of the CMV promoter nucleic acid in cell lines K18.1, G25-10, G25-17 and 43-16 A10 was higher than the background of incomplete deamination, which had been found to be approximately 1%. Methylation in cell line G42-5 was below or maximum at background level. For cell line K18.1 the highest methylation was determined (more than 60%).

Assay setting a) was performed with other universal and methylation specific primer pairs. For the calculation of the fraction of DNA methylated at position 425, the amplification efficiency for all primer pairs was assumed to be 2:

$$mC = 2^{Cp(t)-Cp(m)} * 100 \quad \text{(Formula 5')}$$

with
- mC [%]: fraction of DNA methylated at position 425,
- Cp(t): Cp value obtained with universal primer pair,
- Cp(m): Cp value obtained with methylation specific primer pair.

Table 7 shows a summary of primer pair combinations that have been tested on either cloned DNA templates or on genomic DNA with or without pre-amplification of CMV promoter DNA

TABLE 7

Primer pair combinations.

| Combination | universal | position 425 specific |
|---|---|---|
| 1 | 239 + 237 | 239 + 266 |
| 2 | 263 + 237 | 263 + 266 |
| 3 | 264 + 237 | 264 + 266 |
| 4 | 239 + 237 | 239 + 267 |
| 5 | 263 + 237 | 263 + 267 |
| 6 | 264 + 237 | 266 + 267 |

EXAMPLE 7

Methylation of Human CMV Immediate Early Promoter/Enhancer and Prediction of Production Instability of Recombinant CHO Cell Line CHO-K1 cells were transfected with a plasmid coding for a human IgG4 antibody and stable clones were selected using the DHFR/MTX system. High producing parental clones were subcloned by limiting dilution. MTX was kept in the growth medium during the complete cell line generation process. 16 subclones from 10 parental clones were selected.

Selected cells were re-cultivated with 250 nM MTX. As soon as they showed stable growth, they were tested for long term production stability over 60 to 80 generations in the presence and in the absence of MTX. The relative alteration of the SPR over 60 generations was calculated. Methylation of C425 was determined at the beginning of the study with cells grown with MTX and at the end of the study from cells that had been cultivated without MTX.

Figure 11A:
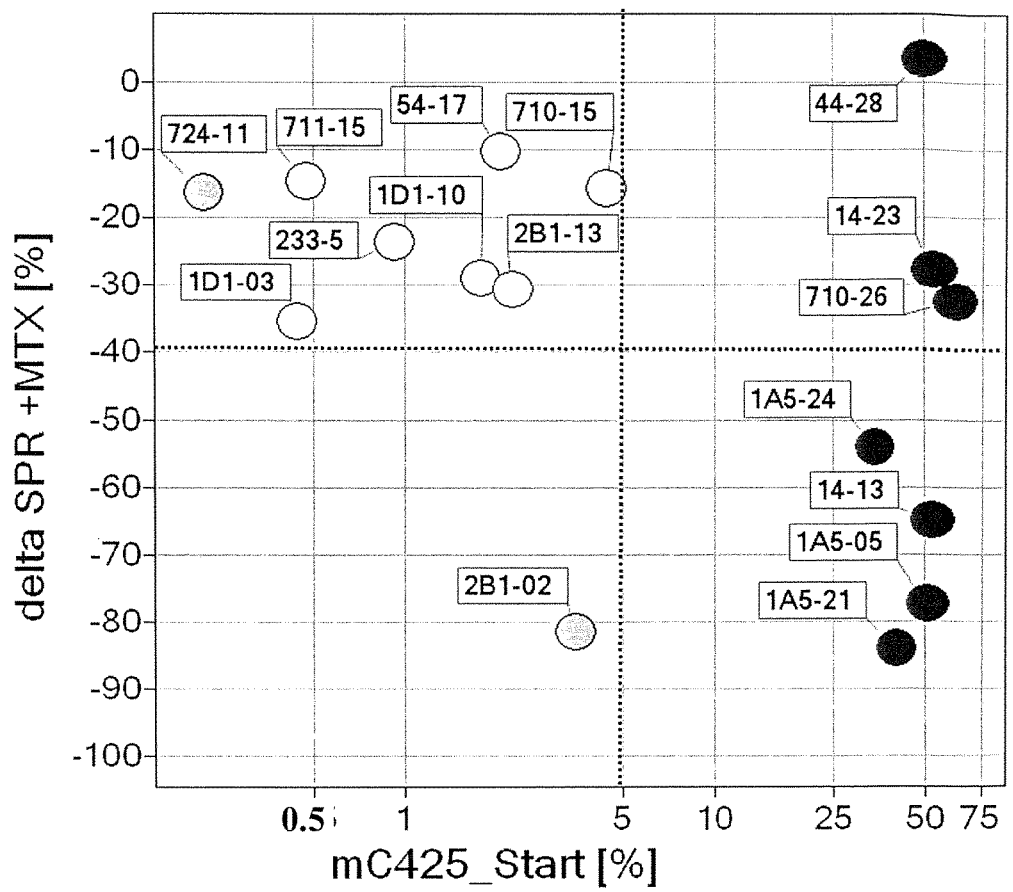
FIGS. 11A-B Correlation of the degree of methylation at C425 before long-term cultivation and the relative alteration of the SPR after 60 generations cultivation with 250 nM MTX (FIG. 11A) or without MTX (FIG. 11B).
Figure 11B:
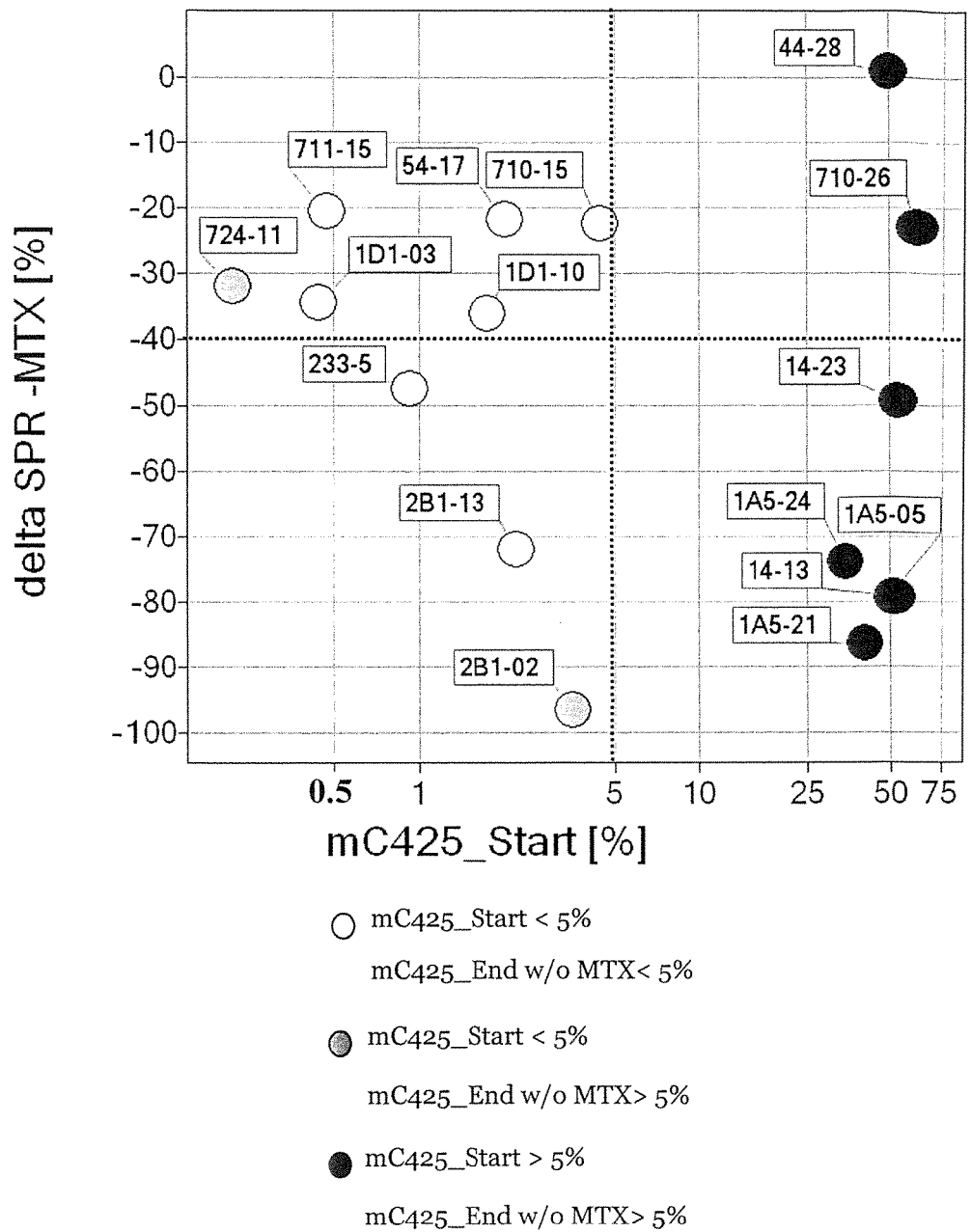

C425 methylation at start of the study was plotted against the relative alteration of the SPR in the presence (FIG. 11A) and in the absence of MTX (FIG. 11B). The majority of clones with less than 5% methylation at C425 can be found in the fraction of stable clones (less than 40% decrease of SPR with or without MTX), whereas the majority of clones with more than 5% methylation at C425 clustered in the fraction of instable clones. This was independent of weather methylation was correlated with stability in the presence or in the absence of MTX (see also table 8). Most of the stable clones, that lose less than 20% productivity with MTX and less than 30% productivity without MTX, exhibit less than 5% C425 methylation.

TABLE 8

Correlation of methylation with stability in the presence or in the absence of MTX (A) and plasmid copy number (B).

| A - 16 clones | number of clones with methylation at C425 at start less than 5% | number of clones with methylation at C425 at start more than 5% |
|---|---|---|
| SPR$_{rel}$_End ≥60% (cultivation in the presence of MTX) | 8 | 3 |
| SPR$_{rel}$_End <60% (cultivation in the presence of MTX) | 1 | 4 |
| SPR$_{rel}$_End ≥60% (cultivation in the absence of MTX) | 6 | 2 |
| SPR$_{rel}$_End <60% (cultivation in the absence of MTX) | 3 | 5 |

| B - 16 clones | plasmid copy number less than 10 | plasmid copy number equal to or more than 10 |
|---|---|---|
| SPR$_{rel}$_End ≥60% (cultivation in the presence of MTX) | 7 | 4 |
| SPR$_{rel}$_End <60% (cultivation in the presence of MTX) | 0 | 5 |
| SPR$_{rel}$_End ≥60% (cultivation in the absence of MTX) | 6 | 2 |
| SPR$_{rel}$_End <60% (cultivation in the absence of MTX) | 1 | 7 |

This finding shows that the determination of C425 methylation can be used as a predictive marker to determine the stability of polypeptide expression in generated cell clones and thereby allowing the selection of stable clones with stable productivity during cell line development. It has been found that C425 methylation of 5% or less is a suitable criterion for the selection of stable cell clones.

Figure 12:
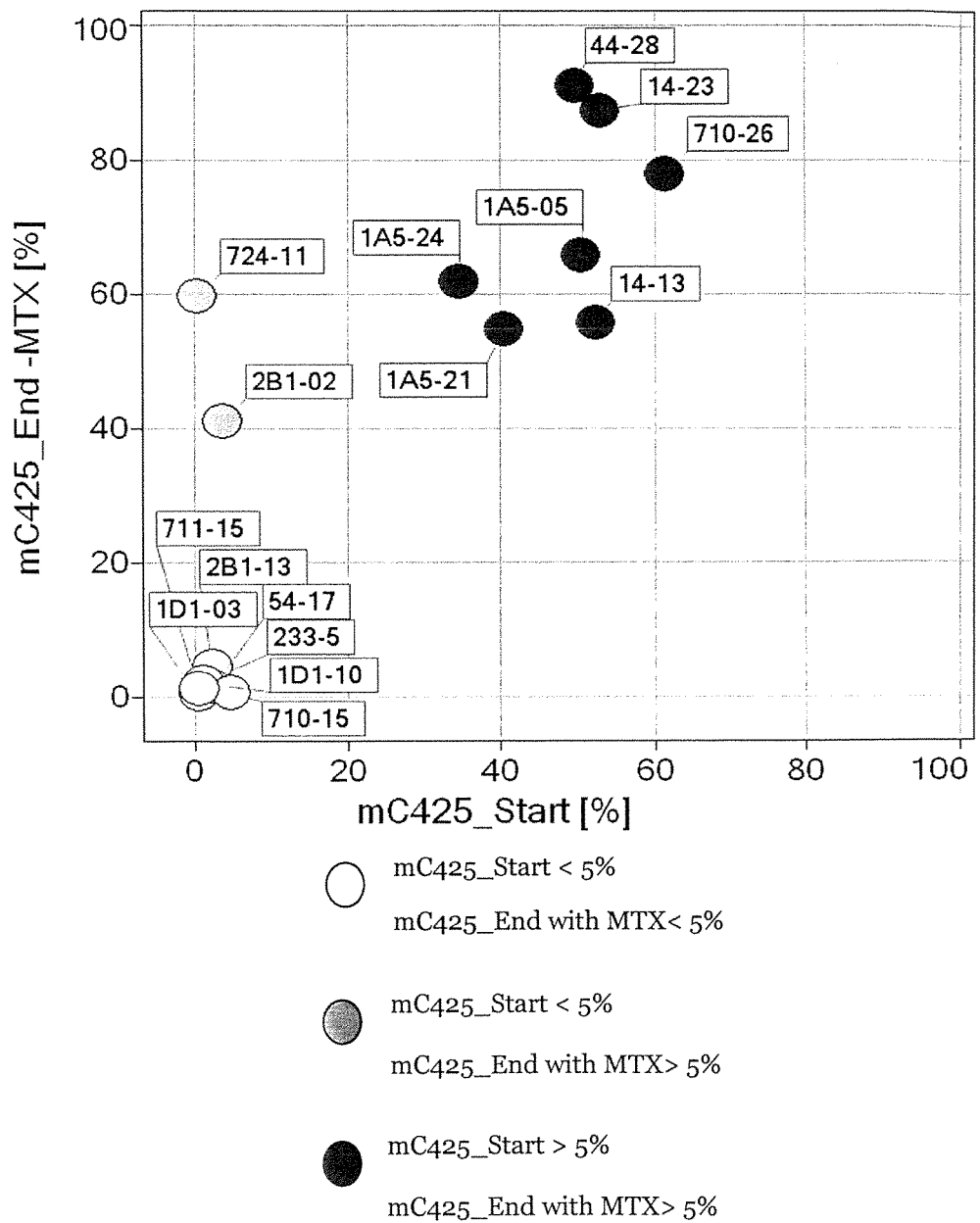
FIG. 12 Correlation of the degree of methylation at C425 before long-term cultivation and the degree of methylation after 60 generations cultivation with 250 nM MTX.

It has further been found that two intermediately stable cell clones as well as two very instable clones that were non-methylated at the beginning of the study rise above 5% in methylation during stability testing without MTX (see also FIG. 12). This shows that the fraction of cell clones that are falsely predicted as stable (false negative cell clones) can be reduced by cultivating them for some time in the absence of MTX before testing.

Figure 13:
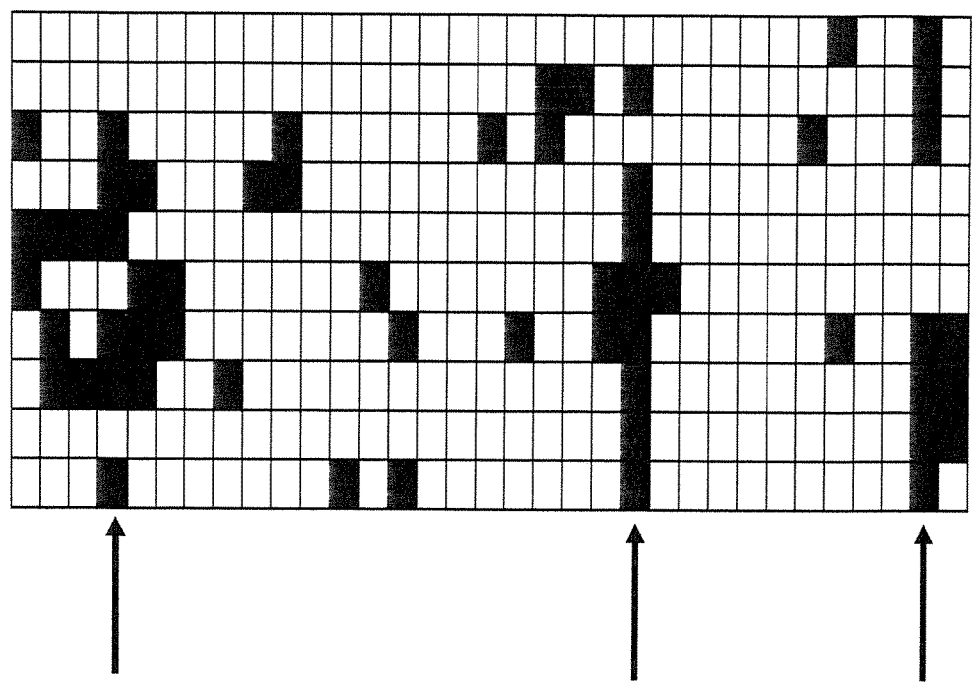
FIG. 13 Schematic representation of methylated CpG sites within hCMV-MIE promoter/enhancer DNA from clone 44-28. Methylated sites are shown in black. Nucleotide position 425 is highlighted by an arrow. Methylation of all CpG sites: 18%; methylation at C425: 80%; methylation at C591: 70%; methylation at C96: 60%.

In order to confirm C425 methylation by a second method, we performed bisulfite sequencing with highly methylated clone 44-28 (FIG. 13). The degree of methylation at C425 was found to be 80%. This was consistent with the result of methylation specific PCR, considering the variation of both assays. As with clones K18.1 and 43-16 A10 (FIGS. 4A and 4E), C425 was most often methylated among all CpG sites within the human CMV immediate early promoter/enhancer DNA. Other methylation events clustered at the 5' end and the 3' end. The average degree of methylation at all sites was 18%.

EXAMPLE 8

Early Methylation Co-Incides with High Transgene Copy Numbers

We determined the integrated copies of immunoglobulin light and heavy chain genes at the beginning and at the end of stability testing using a multiplex qPCR assay based on the TaqMan principle. Two primer sets consisting of a forward primer, a reverse primer and a hydrolysis probe were used: the one being specific for the human kappa chain gene, the other being specific for human gamma heavy chain genes. To allow determination of absolute copy numbers, the linearized expression plasmid, which had been used for transfection, was used as a standard. Equal amplification efficiency of samples and standard were assured.

For qPCR, the LightCycler® 480 II system was employed (Roche Diagnostics GmbH, Mannheim, Germany) and samples were prepared using the LightCycler® 480 Probes Master (Roche Diagnostics GmbH, Mannheim, Germany).

5 µl template solution containing 50 ng genomic DNA was combined with 15 µl PCR master mix in the well of a 96-well microtiter plate. In case of the standard, the template solution contained $2.5 \times 10^7$, $2.5 \times 10^6$, $2.5 \times 10^5$, $2.5 \times 10^4$ and $2.5 \times 10^3$ copies of the corresponding linearized plasmid DNA. 15 µl PCR master mix comprised:

10 µl LightCycler® 480 Probes Master
1 µl forward primer #133 (10 pmol/µl)
1 µl reverse primer #132 (10 pmol/µl)
0.5 µl probe #166 (10 pmol/µl)
1 µl forward primer #178 (10 pmol/µl)
1 µl reverse primer #180 (10 pmol/µl)
0.5 µl probe #185 (10 pmol/µl)

The plate was sealed with a LightCycler® 480 sealing foil (Roche Diagnostics GmbH, Mannheim, Germany) and centrifuged at 1,500 g for 2 minutes. Afterwards the plate was mounted into the LightCycler® 480 system and subjected to qPCR. Each sample was tested in triplicate, standards were run in quadruplicate.

PCR conditions were as follows:

| step | | No. of cycles | T [° C.] | t [min:s] | ramp rate [° C. s − 1] | acquisition |
|---|---|---|---|---|---|---|
| denaturation | | 1 | 95 | 10:00 | 4.40 | — |
| real-Time PCR | denaturation | 45 | 95 | 00:10 | 4.40 | — |
| | annealing | | 60 | 00:05 | 2.20 | — |
| | elongation | | 72 | 00:01 | 4.40 | single |
| cooling | | 1 | 37 | 01:00 | 2.2 | |

The collection and analysis of the data was performed using the LightCycler® 480 software version 1.5. Basically, mean Cp values of the plasmid standard dilutions were plotted against the respective gene copy numbers to generate a standard curve from which the number of transgenes in the sample was extrapolated.

The number transgenes per cell was calculated assuming that the average DNA content per cell is jpg:

$$N_c = N_s / 50000 * 6$$

$N_c$: number of transgene copies per cell $N_s$: number of transgene copies in the sample

TABLE 9

Primer sequences.

| Primer no. | Primer sequences (5'->3') | SEQ ID NO: |
|---|---|---|
| 133 | TCACAGAGCAGGACAGCAAG | 26 |
| 132 | GACTTCGCAGGCGTAGACTT | 27 |
| 166 | (FAM-AGCACCTACAGCCTCAGCAGCACC-BHQ1) | 28 |
| 178 | CGAACCGGTGACGGTGT | 29 |
| 180 | GAGGGCACGGTCACCAC | 30 |
| 185 | (Cy5-CACACCTTCCCGGCTGTCCTACAG-BHQ3) | 31 |

Figure 14:
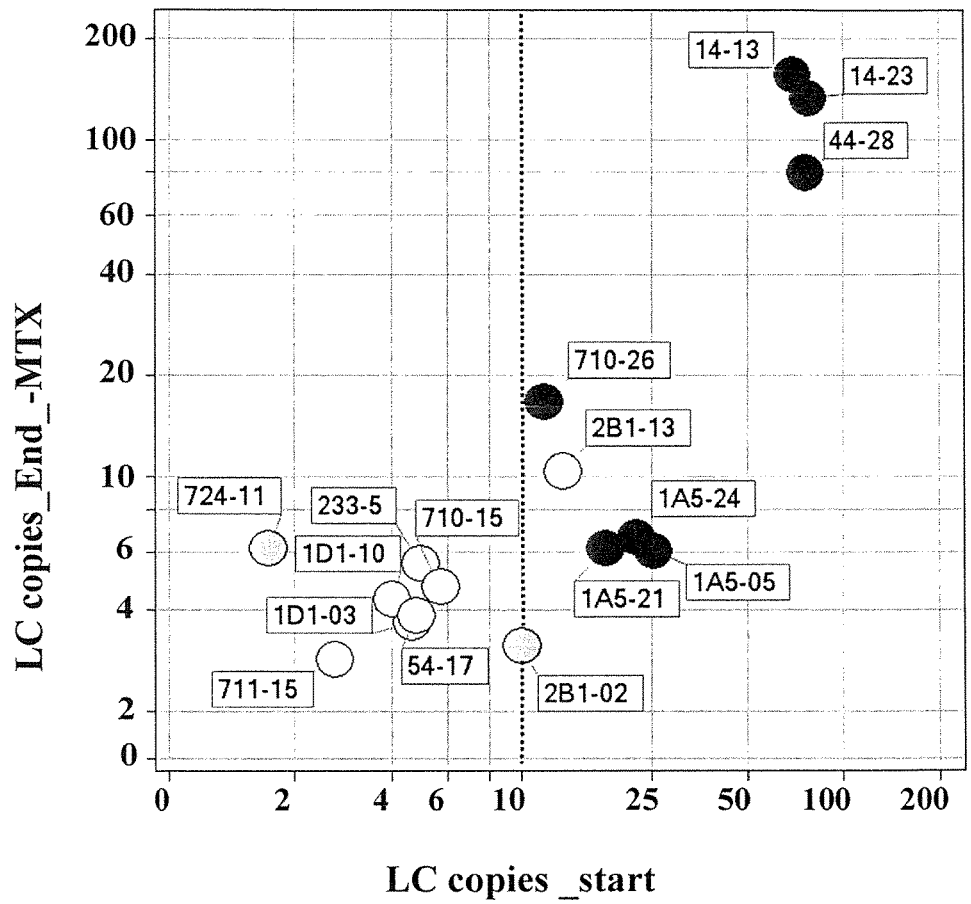
FIG. 14 Light chain gene copy numbers before and after stability testing without MTX.
Figure 15A:
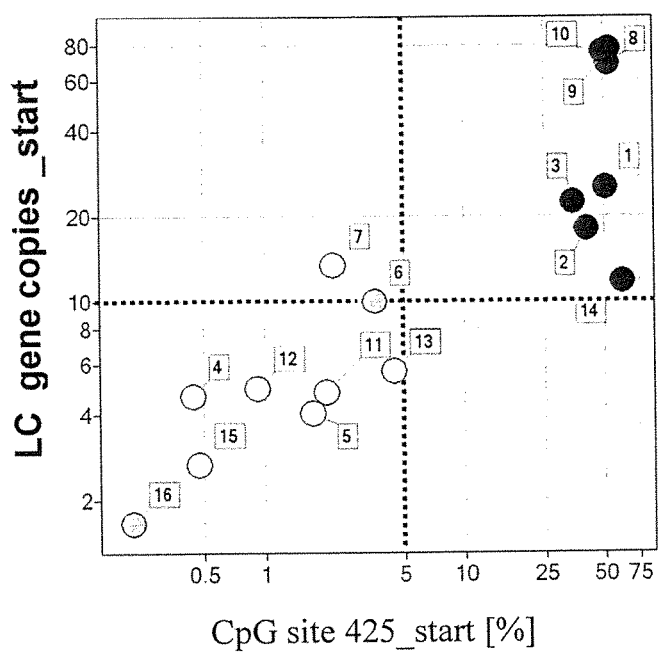
FIGS. 15A-B Light chain gene copy numbers (FIG. 15A) and hCMV-MIE methylation of antibody producing CHO cell lines (FIG. 15B).
Figure 15B:
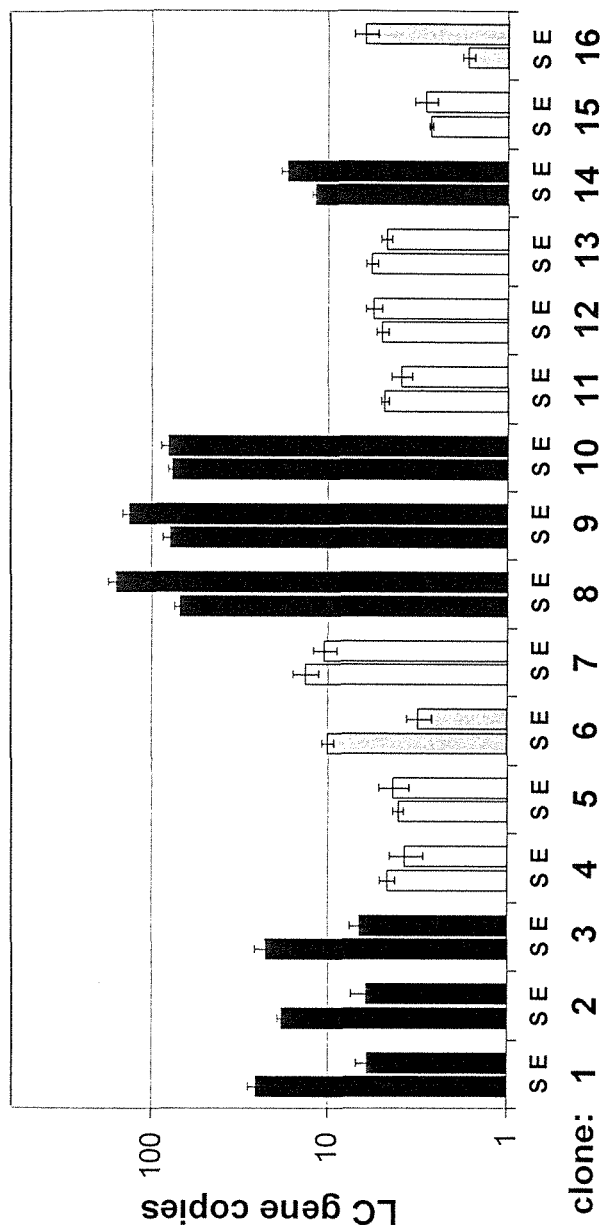

FIG. 14 depicts the light chain gene copy numbers of methylated and non-methylated cells before and after stability testing. Not surprisingly, identical copy numbers were found the heavy chain gene because the cells had been transfected with a double gene vector carrying both genes (data not shown). Early methylation i.e. methylation before stability testing was exclusively found with cells carrying more than 10 transgene copies whereas some clones with less than 10 transgene copies acquired methylation during stability testing. As a consequence, selecting clones with low transgene copy numbers before stability testing equally enriches clones with stable productivity (Table 10).

TABLE 10

Correlation of transgene copies with stability in the presence or in the absence of MTX.

| 16 clones | Plasmid copies <10 | Plasmid copies ≥10 |
|---|---|---|
| $qP_{rel}$_End +MTX ≥60% | 7 | 4 |
| $qP_{rel}$_End +MTX <60% | 0 | 5 |
| $qP_{rel}$_End −MTX ≥60% | 6 | 2 |
| $qP_{rel}$_End −MTX <60% | 1 | 7 |

We further observed, that production instability was not generally associated with a loss of transgene copies. Clones 1A5-05, 1A5-21, 1A5-24 and 2B1-02 lost transgene copies, 2B-13 was stable and 14-13 as well as 14-23 increased in gene copies (see also FIG. 11B).

The invention claimed is:

1. A method for enriching cell clones for expression of a polypeptide comprising the following steps:
   a) determining for each of at least one cell clone in a mixture of cell clones, which comprises a nucleic acid comprising a structural gene encoding the polypeptide operably linked to a promoter nucleic acid that has the nucleic acid sequence of SEQ ID NO: 01, the methylation frequency of a CpG-site at position 425 of SEQ ID NO: 01 based on the methylation measured for at least 10 copies of the nucleic acid or in at least 10 cells obtained from a cultivation of each cell clone;
   b) selecting from the mixture a cell clone in which the methylation frequency as determined is below 5% and not selecting from the mixture a cell clone in which the methylation frequency as determined is more than 5%;
   c) cultivating the selected cell clone for long-term cultivation of 35 to 70 generations; and
   d) recovering the polypeptide from the selected cell clone after the long-term cultivation thereby stably producing the polypeptide.

2. The method of claim 1, wherein the determining step a) comprises the following steps:
   1) isolating the DNA from each of the cell clones;
   2) performing for each isolated DNA individually a polymerase chain reaction and
   3) determining the methylation frequency of the CpG-site.

3. The method of claim 2, wherein the DNA isolated from each of the cell clones is individually digested with a restriction enzyme and the polymerase chain reaction for each of the digested DNA is performed with a methylation specific primer and a universal primer.

4. The method of claim 2, wherein the polymerase chain reaction is performed with primers and the primers are independently of each other selected from the group consisting of SEQ ID NO: 06, 07, and SEQ ID NO 09-20.

5. The method of claim 2, wherein the polymerase chain reaction is performed with primers and the primers are selected from the group consisting of SEQ ID NO: 09, 11, 14, 15, 17, 18 and 19.

6. The method of claim 2, wherein the polymerase chain reaction is performed with primers and the primers are a universal primer pair that have the sequence of SEQ ID NO: 09 and 11 and a methylation specific primer pair that have the sequence of SEQ ID NO: 11 and 18.

7. The method of claim 1 or 2, characterized in that the selected cell clone is a chinese hamster ovary (CHO) cell clone.

* * * * *

SEQUENCE LISTING

<160> NUMBER OF SEQ ID NOS: 31

<210> SEQ ID NO 1
<211> LENGTH: 603
<212> TYPE: DNA
<213> ORGANISM: Human cytomegalovirus

<400> SEQUENCE: 1

| | | | | | | |
|---|---|---|---|---|---|---|
| atgttgacat | tgattattga | ctagttatta | atagtaatca | attacggggt | cattagttca | 60 |
| tagcccatat | atggagttcc | gcgttacata | acttacggta | aatggcccgc | ctggctgacc | 120 |
| gcccaacgac | ccccgcccat | tgacgtcaat | aatgacgtat | gttcccatag | taacgccaat | 180 |
| agggactttc | cattgacgtc | aatgggtgga | gtatttacgg | taaactgccc | acttggcagt | 240 |
| acatcaagtg | tatcatatgc | caagtacgcc | ccctattgac | gtcaatgacg | gtaaatggcc | 300 |
| cgcctggcat | tatgcccagt | acatgacctt | atgggacttt | cctacttggc | agtacatcta | 360 |
| cgtattagtc | atcgctatta | gcatggtgat | gcggttttgg | cagtacatca | atgggcgtgg | 420 |
| atagcggttt | gactcacggg | gatttccaag | tctccacccc | attgacgtca | atgggagttt | 480 |
| gttttggcac | caaaatcaac | gggactttcc | aaaatgtcgt | aacaactccg | ccccattgac | 540 |
| gcaaatgggc | ggtaggcgtg | tacggtggga | ggtctatata | agcagagctc | gtttagtga | 600 |
| acg | | | | | | 603 |

<210> SEQ ID NO 2
<211> LENGTH: 603
<212> TYPE: DNA
<213> ORGANISM: Human cytomegalovirus

<400> SEQUENCE: 2

| | | | | | | |
|---|---|---|---|---|---|---|
| atgttgatat | tgattattga | ttagttatta | atagtaatta | attacggggt | tattagttta | 60 |
| tagtttatat | atggagtttc | gcgttatata | atttacggta | aatggttcgt | ttggttgatc | 120 |
| gtttaacgat | tttcgtttat | tgacgttaat | aatgacgtat | gtttttatag | taacgttaat | 180 |
| agggattttt | tattgacgtt | aatgggtgga | gtatttacgg | taaattgttt | atttggtagt | 240 |
| atattaagtg | tattatatgt | taagtacgtt | ttttattgac | gttaatgacg | gtaaatggtt | 300 |
| cgtttggtat | tatgtttagt | atatgatttt | atgggatttt | tttatttggt | agtatattta | 360 |
| cgtattagtt | atcgttatta | gtatggtgat | gcggttttgg | tagtatatta | atgggcgtgg | 420 |
| atagcggttt | gatttacggg | gattttttaag | ttttttatttt | attgacgtta | atgggagttt | 480 |
| gttttggtat | taaaattaac | gggatttttt | aaaatgtcgt | aataatttcg | ttttattgac | 540 |
| gtaaatgggc | ggtaggcgtg | tacggtggga | ggtttatata | agtagagttt | cgtttagtga | 600 |
| acg | | | | | | 603 |

<210> SEQ ID NO 3
<211> LENGTH: 603
<212> TYPE: DNA
<213> ORGANISM: Human cytomegalovirus

<400> SEQUENCE: 3

| | | | | | | |
|---|---|---|---|---|---|---|
| atgttgatat | tgattattga | ttagttatta | atagtaatta | attatggggt | tattagttta | 60 |
| tagtttatat | atggagtttt | gtgttatata | atttatggta | aatggtttgt | ttggttgatt | 120 |
| gtttaatgat | tttgtttat | tgatgttaat | aatgatgtat | gtttttatag | taatgttaat | 180 |
| agggattttt | tattgatgtt | aatgggtgga | gtatttatgg | taaattgttt | atttggtagt | 240 |
| atattaagtg | tattatatgt | taagtatgtt | ttttattgat | gttaatgatg | gtaaatggtt | 300 |

```
tgtttggtat tatgtttagt atatgattt  atgggattt  tttattggt agtatattta    360 tgtattagtt attgttatta gtatggtgat gtggttttgg tagtatatta atgggtgtgg    420
atagtggttt gatttatggg gattttaag  tttttattt  attgatgta atgggagttt    480 gttttggtat taaaattaat gggatttttt aaaatgttgt ataatttg  ttttattgat    540 gtaaatgggt ggtaggtgtg tatggtggga ggtttatata agtagagttt gtttagtga    600 atg                                                                 603

<210> SEQ ID NO 4
<211> LENGTH: 603
<212> TYPE: DNA
<213> ORGANISM: Human cytomegalovirus

<400> SEQUENCE: 4
cgtttattaa acggagttt  gtttatatag attttttatc gtatacgtt  atcgtttatt     60 tgcgttaatg gggcggagtt gttacgatat tttggaaagt ttcgttgatt ttggtgttaa    120
aataaatttt tattgacgtt aatggggtgg agatttggaa attttcgtga gttaaatcgt    180
tatttacgtt tattgatgta ttgttaaaat cgtattatta tgttaatagc gatgattaat    240
acgtagatgt attgttaagt aggaaagttt ataaggtta  tgtattgggt ataatgttag    300
gcgggttatt tatcgttatt gacgttaata ggggcgtat  ttggtatatg atatatttga    360
tgtattgtta agtgggtagt ttatcgtaaa tattttattt attgacgtta atggaaagtt    420
tttattggcg ttattatggg aatatacgtt attattgacg ttaatgggcg ggggtcgttg    480
ggcggttagt taggcgggtt atttatcgta agttatgtaa cgcggaattt tatatatggg    540
ttatgaatta atgatttcgt aattgattat tattaataat tagttaataa ttaatgttaa    600
tat                                                                 603

<210> SEQ ID NO 5
<211> LENGTH: 603
<212> TYPE: DNA
<213> ORGANISM: Human cytomegalovirus

<400> SEQUENCE: 5
tgtttattaa atggagttt  gtttatatag atttttatt  gtatatgttt attgtttatt     60
tgtgttaatg gggtggagtt gttatgatat tttggaaagt tttgttgatt ttggtgttaa    120
aataaatttt tattgatgtt aatggggtgg agatttggaa attttgtga  gttaaattgt    180 tatttatgtt tattgatgta ttgttaaaat tgtattatta tgttaatagt gatgattaat    240
atgtagatgt attgttaagt aggaaagttt ataaggtta  tgtattgggt ataatgttag    300
gtgggttatt tattgttatt gatgttaata ggggtgtat  ttggtatatg atatatttga    360
tgtattgtta agtgggtagt ttattgtaaa tattttattt attgatgtta atggaaagtt    420
tttattggtg ttattatggg aatatatgtt attattgatg ttaatgggtg ggggttgttg    480
ggtggttagt taggtgggtt atttattgta agttatgtaa tgtggaattt tatatatggg    540
ttatgaatta atgattttgt aattgattat tattaataat tagttaataa ttaatgttaa    600
tat                                                                 603

<210> SEQ ID NO 6
<211> LENGTH: 24
<212> TYPE: DNA
<213> ORGANISM: Artificial Sequence
<220> FEATURE:
```

<223> OTHER INFORMATION: Primer 227

<400> SEQUENCE: 6
atgttgatat tgattattga ttag                                              24

<210> SEQ ID NO 7
<211> LENGTH: 24
<212> TYPE: DNA
<213> ORGANISM: Artificial Sequence
<220> FEATURE:
<223> OTHER INFORMATION: Primer 228

<400> SEQUENCE: 7
tatgggattt ttttatttgg tagt                                              24

<210> SEQ ID NO 8
<211> LENGTH: 24
<212> TYPE: DNA
<213> ORGANISM: Artificial Sequence
<220> FEATURE:
<223> OTHER INFORMATION: Primer 229

<400> SEQUENCE: 8
actcctctcc caaaactaaa tcta                                              24

<210> SEQ ID NO 9
<211> LENGTH: 21
<212> TYPE: DNA
<213> ORGANISM: Artificial Sequence
<220> FEATURE:
<223> OTHER INFORMATION: Primer 237

<400> SEQUENCE: 9
ccaaaacaaa ctcccattaa c                                                 21

<210> SEQ ID NO 10
<211> LENGTH: 24
<212> TYPE: DNA
<213> ORGANISM: Artificial Sequence
<220> FEATURE:
<223> OTHER INFORMATION: Primer 238

<400> SEQUENCE: 10
ggggttatta gtttatagtt tata                                              24

<210> SEQ ID NO 11
<211> LENGTH: 28
<212> TYPE: DNA
<213> ORGANISM: Artificial Sequence
<220> FEATURE:
<223> OTHER INFORMATION: Primer 239

<400> SEQUENCE: 11
tggtattatg tttagtatat gatttat                                           28

<210> SEQ ID NO 12
<211> LENGTH: 25
<212> TYPE: DNA
<213> ORGANISM: Artificial Sequence
<220> FEATURE:
<223> OTHER INFORMATION: Primer 240

<400> SEQUENCE: 12 ggatttttt atttggtagt atatt                                              25

```
<210> SEQ ID NO 13
<211> LENGTH: 21
<212> TYPE: DNA
<213> ORGANISM: Artificial Sequence
<220> FEATURE:
<223> OTHER INFORMATION: Primer 254

<400> SEQUENCE: 13
aaatccccgt aaatcaaacc g                                              21

<210> SEQ ID NO 14
<211> LENGTH: 26
<212> TYPE: DNA
<213> ORGANISM: Artificial Sequence
<220> FEATURE:
<223> OTHER INFORMATION: Primer 263

<400> SEQUENCE: 14 gggattttttt tatttggtag tatatt                                        26

<210> SEQ ID NO 15
<211> LENGTH: 25
<212> TYPE: DNA
<213> ORGANISM: Artificial Sequence
<220> FEATURE:
<223> OTHER INFORMATION: Primer 264

<400> SEQUENCE: 15
tatgggattt ttttatttgg tagta                                          25

<210> SEQ ID NO 16
<211> LENGTH: 19
<212> TYPE: DNA
<213> ORGANISM: Artificial Sequence
<220> FEATURE:
<223> OTHER INFORMATION: Primer 265

<400> SEQUENCE: 16
atccccgtaa atcaaaccg                                                 19

<210> SEQ ID NO 17
<211> LENGTH: 18
<212> TYPE: DNA
<213> ORGANISM: Artificial Sequence
<220> FEATURE:
<223> OTHER INFORMATION: Primer 266

<400> SEQUENCE: 17
tccccgtaaa tcaaaccg                                                  18

<210> SEQ ID NO 18
<211> LENGTH: 17
<212> TYPE: DNA
<213> ORGANISM: Artificial Sequence
<220> FEATURE:
<223> OTHER INFORMATION: Primer 267

<400> SEQUENCE: 18
ccccgtaaat caaaccg                                                   17

<210> SEQ ID NO 19
<211> LENGTH: 17
<212> TYPE: DNA
<213> ORGANISM: Artificial Sequence
<220> FEATURE:
<223> OTHER INFORMATION: Primer 268
```

<400> SEQUENCE: 19
cccgtaaatc aaaccgc                                                    17

<210> SEQ ID NO 20
<211> LENGTH: 21
<212> TYPE: DNA
<213> ORGANISM: Artificial Sequence
<220> FEATURE:
<223> OTHER INFORMATION: Primer 262

<400> SEQUENCE: 20
aaatccccrt aaatcaaacc g                                               21

<210> SEQ ID NO 21
<211> LENGTH: 628
<212> TYPE: DNA
<213> ORGANISM: Artificial Sequence
<220> FEATURE:
<223> OTHER INFORMATION: Template #11

<400> SEQUENCE: 21
atgttgatat tgattattga ttagttatta atagtaatta attatggggt tattagttta    60
tagttcatat atggagtttt gtgttatata atttatggta aatggtttgt ttggttgatt   120
gtttaatgat ttttgtttat tgatgttaat aatgatgtat gttttatag taatgttaat    180
agggattttt tattgatgtt aatgggtgga gtatttatgg taaattgttt atttggtagt   240
atattaagtg tattatatgt taagtatgtt ttttattgat gttaatgatg gtaaatggtt   300
tgtttggtat tatgtttagt atatgatttt atgggatttt tttatttggt agtatattta   360
tgtattagtt attgttatta gtatggtgat gtggttttgg tagtatatta atgggtgtgg   420
atagtggttt gatttatggg gattttttaag ttttttatttt attgatgtta atgggagttt   480
gttttggtat taaaattaat gggatttttt aaaatgttgt ataaattttg ttttattgat   540
gtaaatgggt ggtaggtgtg tatggtggga ggtttatata agtagagttt tgtttagtga   600
atgttagatt tagttttggg agaggagt                                       628

<210> SEQ ID NO 22
<211> LENGTH: 629
<212> TYPE: DNA
<213> ORGANISM: Artificial Sequence
<220> FEATURE:
<223> OTHER INFORMATION: Template #62

<400> SEQUENCE: 22
atgttgatat tgattattga ttagttatta atagtaatta attatggggt tattagttta    60
tagttyatat atggagttty gygttatata atttatgrta aatggtttgt ttggttgatt   120
gtttaatgat ttttgtttat tgatgttaat aatgatgtat gttttatag taatgttaat    180
agggattttt tattgatgtt aatgggtgga gtatttatgg taaaytgttt atttggtagt   240
atattaagtg tattatatgt taagtatgtt ttttattgat gttaatgatg gtaaatggtt   300
tgtttggtat tatgtttagt atatgatttt atgggatttt tttatttggt agtatattta   360
ygtattagtt atygttatta gtatggtgat gtggttttgg tagtatatta atgggcgtgg   420
atagcggttt gatttacggg gattttttaag ttttttatttt attgatgtta atgggagttt   480
gttttggtat taaaattaat gggatttttt aaaatgttgt ataaattttg ttttattgat   540
gtaaatgggt ggtaggtgtg tacggtggga ggtttatata agtagagttt cgtttagtga   600
atcgttagat ttagttttgg gagaggagt                                      629

<210> SEQ ID NO 23
<211> LENGTH: 629
<212> TYPE: DNA
<213> ORGANISM: Artificial Sequence
<220> FEATURE:
<223> OTHER INFORMATION: Template #01

<400> SEQUENCE: 23

| | | | | | |
|---|---|---|---|---|---|
| atgttgatat | tgattattga | ttagttatta | atagtaatta | attatggggt | tattagttta | 60 |
| tagtttatat | atggagtttt | gtgttatata | atttatggta | aatggtttgt | ttggttgatt | 120 |
| gtttaatgat | ttttgtttat | tgatgttaat | aatgatgtat | gtttttatag | taatgttaat | 180 |
| agggattttt | tattgatgtt | aatgggtgga | gtatttatgg | taaattgttt | atttggcagt | 240 |
| atattaagtg | tattatatgt | taagtatgtt | ttttattgat | gttaatgatg | gtaaatggtt | 300 |
| cgtttggtat | tatgtttagt | atatgatttt | atgggatttt | tttatttggt | agtatattta | 360 |
| tgtattagtt | attgttatta | gtatggtgat | gtggttttgg | tagtatatta | atgggtgtgg | 420 |
| atagcggttt | gatttatggg | gatttttaag | tttttatttt | attgatgtta | atgggagttt | 480 |
| gttttggtat | taaaattaat | gggatttttt | aaaatgttgt | aataatttg | ttttattgat | 540 |
| gtaaatgggt | ggtaggtgtg | tacggtggga | ggtttatata | agtagagttt | tgtttagtga | 600 |
| attgttagat | ttagttttgg | gagaggagt | | | | 629 |

<210> SEQ ID NO 24
<211> LENGTH: 629
<212> TYPE: DNA
<213> ORGANISM: Artificial Sequence
<220> FEATURE:
<223> OTHER INFORMATION: Template #04

<400> SEQUENCE: 24

| | | | | | |
|---|---|---|---|---|---|
| atgttgatat | tgattattga | ttagttatta | atagtaatta | attatggggt | tattagttta | 60 |
| tagtttatat | atggagtttt | gtgttatata | atttatggta | aatggtttgt | ttggttgatt | 120 |
| gtttaatgat | ttttgtttat | tgatgttaat | aatgatgtat | gtttttatag | taatgttaat | 180 |
| agggattttt | tattgatgtt | aatgggtgga | gtatttatgg | taaattgttt | atttggtagt | 240 |
| atattaagtg | tattatatgt | taagtatgtt | ttttattgat | gttaatgatg | gtaaatggtt | 300 |
| tgtttggtat | tatgtttagt | atatgatttt | atgggatttt | tttatttggt | agtatattta | 360 |
| tgtattagtt | attgttatta | gtatggtgat | gtggttttgg | tagtatatta | atgggtgtgg | 420 |
| atagtggttt | gatttacggg | gatttttaag | tttttatttt | attgatgtta | atgggagttt | 480 |
| gttttggtat | taaaattaat | gggatttttt | aaaatgttgt | aataatttg | ttttattgat | 540 |
| gtaaatgggt | ggtaggtgtg | tacggtggga | ggtttatata | agtagagttt | tgtttagtga | 600 |
| attgttagat | ttagttttgg | gagaggagt | | | | 629 |

<210> SEQ ID NO 25
<211> LENGTH: 629
<212> TYPE: DNA
<213> ORGANISM: Artificial Sequence
<220> FEATURE:
<223> OTHER INFORMATION: Template #16

<400> SEQUENCE: 25

| | | | | | |
|---|---|---|---|---|---|
| atgttgatat | tgattattga | ttagttatta | atagtaatta | attatggggt | tattagttta | 60 |
| tagtttatat | atggagtttt | gtgttatata | atttacggta | aatggtttgt | ttggttgatc | 120 |

```
gtttaacgat tttcgtttat tgatgttaat aatgacgtat gttttttatag taatgttaat      180 agggattttt tattgatgtt aatgggtgga gtatttacgg taaattgttt atttggtagt      240
atattaagtg tattatatgt taagtatgtt ttttattgat gttaatgatg gtaaatggtt      300
tgtttggtat tatgtttagt atatgatttt atgggacttt cttatttggt agtatattta      360
cgtattagtt atcgttatta gtatggtgat gtggttttgg tagtatatta atgggcgtgg      420
atagcggttt gatttacggg gattttttaag ttttttatttt attgatgtta atgggagttt      480
gttttggtat taaaattaat gggattttttt aaaatgttgt aataatttttg ttttattgat      540 gtaaatgggt ggtaggtgtg tatggtggga ggtttatata agtagagttt tgtttagtga      600
attgttagat ttagttttgg gagaggagt                                         629
```

```
<210> SEQ ID NO 26
<211> LENGTH: 20
<212> TYPE: DNA
<213> ORGANISM: Artificial Sequence
<220> FEATURE:
<223> OTHER INFORMATION: primer 133

<400> SEQUENCE: 26
tcacagagca ggacagcaag                                                   20

<210> SEQ ID NO 27
<211> LENGTH: 20
<212> TYPE: DNA
<213> ORGANISM: Artificial Sequence
<220> FEATURE:
<223> OTHER INFORMATION: primer 132

<400> SEQUENCE: 27
gacttcgcag gcgtagactt                                                   20

<210> SEQ ID NO 28
<211> LENGTH: 24
<212> TYPE: DNA
<213> ORGANISM: Artificial Sequence
<220> FEATURE:
<223> OTHER INFORMATION: primer 166

<400> SEQUENCE: 28
agcacctaca gcctcagcag cacc                                              24

<210> SEQ ID NO 29
<211> LENGTH: 17
<212> TYPE: DNA
<213> ORGANISM: Artificial Sequence
<220> FEATURE:
<223> OTHER INFORMATION: primer 178

<400> SEQUENCE: 29
cgaaccggtg acggtgt                                                      17

<210> SEQ ID NO 30
<211> LENGTH: 17
<212> TYPE: DNA
<213> ORGANISM: Artificial Sequence
<220> FEATURE:
<223> OTHER INFORMATION: primer 180

<400> SEQUENCE: 30
gagggcacgg tcaccac                                                      17
```

```
<210> SEQ ID NO 31
<211> LENGTH: 24
<212> TYPE: DNA
<213> ORGANISM: Artificial Sequence
<220> FEATURE:
<223> OTHER INFORMATION: primer 185

<400> SEQUENCE: 31
cacaccttcc cggctgtcct acag                                              24
```